United States Patent
Canavan et al.

(10) Patent No.: US 12,152,072 B2
(45) Date of Patent: Nov. 26, 2024

(54) METHODS OF TREATING ULCERATIVE COLITIS WITH AN ANTI-IL-23p19 ANTIBODY

(71) Applicant: Eli Lilly and Company, Indianapolis, IN (US)

(72) Inventors: James Benedict Canavan, Indianapolis, IN (US); Stuart William Friedrich, Rondaeu (CA); Kathryn Ann Krueger, Fishers, IN (US); Catherine Milch, Dedham, MA (US); Jay Lawrence Tuttle, San Marcos, CA (US)

(73) Assignee: Eli Lilly and Company

( * ) Notice: Subject to any disclaimer, the term of this patent is extended or adjusted under 35 U.S.C. 154(b) by 273 days.

(21) Appl. No.: 16/981,915

(22) PCT Filed: Mar. 28, 2019

(86) PCT No.: PCT/US2019/024633
§ 371 (c)(1),
(2) Date: Sep. 17, 2020

(87) PCT Pub. No.: WO2019/191464
PCT Pub. Date: Oct. 3, 2019

(65) Prior Publication Data
US 2021/0032325 A1 Feb. 4, 2021

Related U.S. Application Data

(60) Provisional application No. 62/650,314, filed on Mar. 30, 2018.

(51) Int. Cl.
*A61K 39/395* (2006.01)
*A61K 9/00* (2006.01)
*A61P 1/04* (2006.01)
*C07K 16/24* (2006.01)

(52) U.S. Cl.
CPC .......... *C07K 16/244* (2013.01); *A61K 9/0019* (2013.01); *A61P 1/04* (2018.01)

(58) Field of Classification Search
CPC ................ A61P 1/04; A61K 2039/505; A61K 2039/545
See application file for complete search history.

(56) References Cited

U.S. PATENT DOCUMENTS

| | | |
|---|---|---|
| 2007/0009526 A1 | 1/2007 | Benson |
| 2012/0282269 A1 | 11/2012 | Barrett et al. |
| 2017/0002060 A1 | 1/2017 | Bolen |
| 2019/0269757 A1* | 9/2019 | Adedokun .............. A61P 37/06 |

FOREIGN PATENT DOCUMENTS

WO 2010/062663 A1 6/2010

OTHER PUBLICATIONS

Clinical Trial NCT02589665 (v49, Jan. 19, 2018).*
Allocca, et al., "Evolving strategies and goals of treatment in ulcerative colitis," Bailliere's Best Practice and Research. Clinical Gastroenterology, vol. 32-33 (Feb. 2018), pp. 1-2.
El-Bassat, et al., :Interleukin-23p19 expression in patients with ulcerative colitis and its relation to disease severity. Advances in Digestive Medicine, vol. 3, No. 3, pp. 88-94 (Sep. 8, 2015).

* cited by examiner

*Primary Examiner* — Dong Jiang
(74) *Attorney, Agent, or Firm* — Dipa Patel

(57) ABSTRACT

The present invention generally relates to the treatment of ulcerative colitis with an anti-IL-23p19 antibody, in particular dosage regimens for the treatment of the disease.

7 Claims, 5 Drawing Sheets

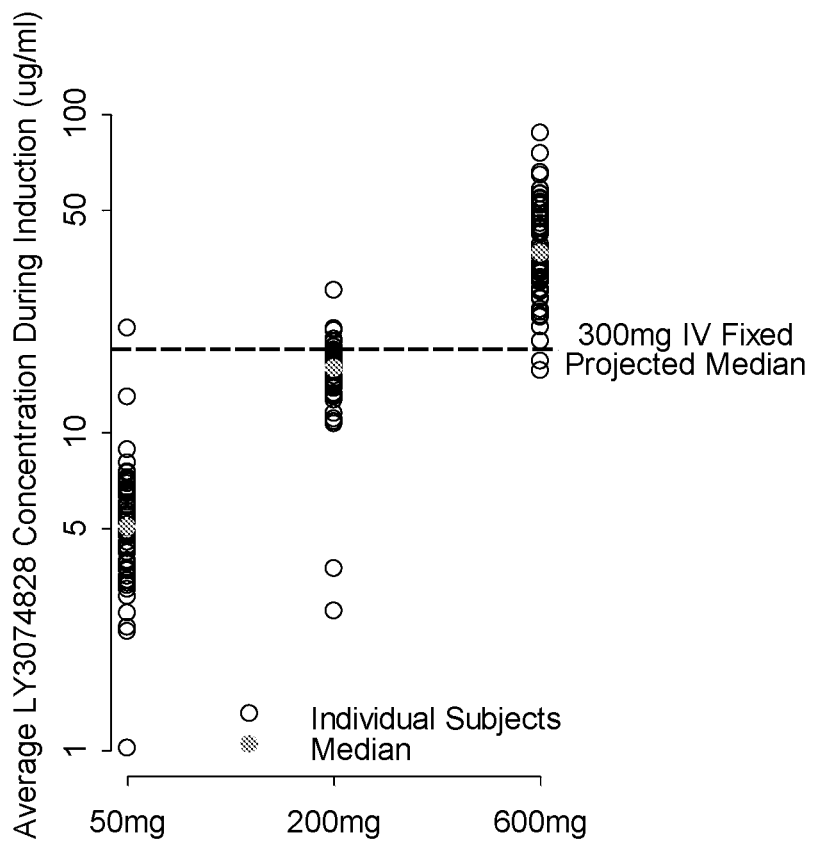
Abbreviations: IV = intravenous.
Note: Dashed line represents where the median average concentration would be expected for a 300-mg fixed IV dose. The overall average doses in the 50-mg and 200-mg cohorts during induction were 100 mg and 250 mg, respectively.
Figure 1: Population PK model-estimated average serum concentrations of mirikizumab

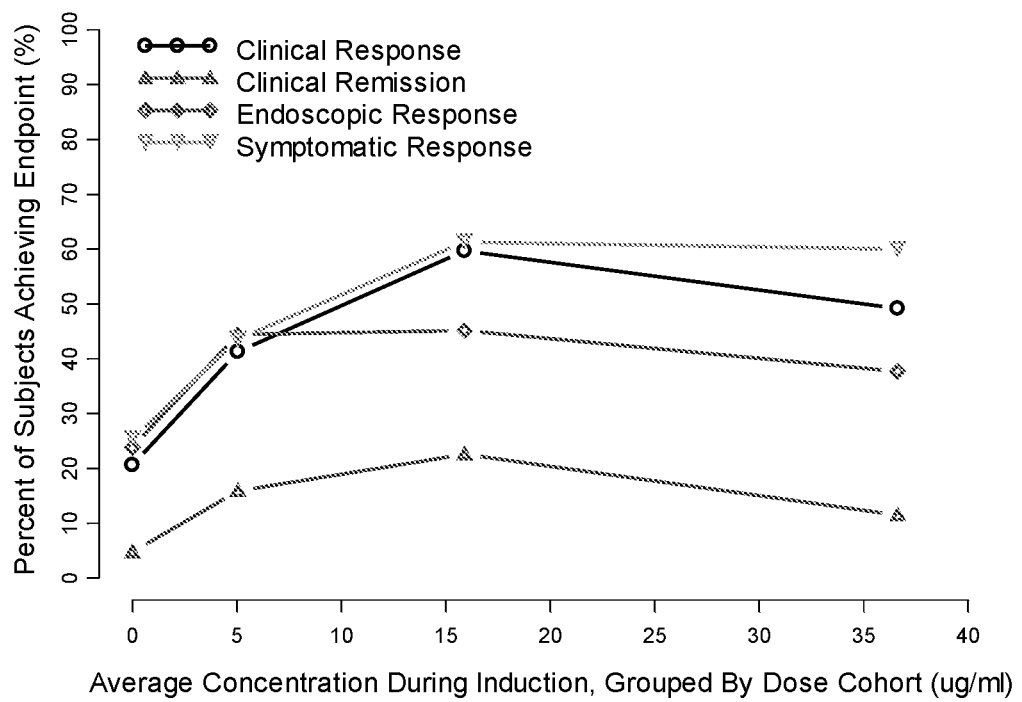
Note: Concentration points are at the median of the PK model-estimated average concentration in the placebo, 50-mg, 200-mg, and 600-mg groups from left to right.
Figure 2: Rates at Week 12 for induction endpoints of interest relative to average concentration of mirikizumab in each dose group

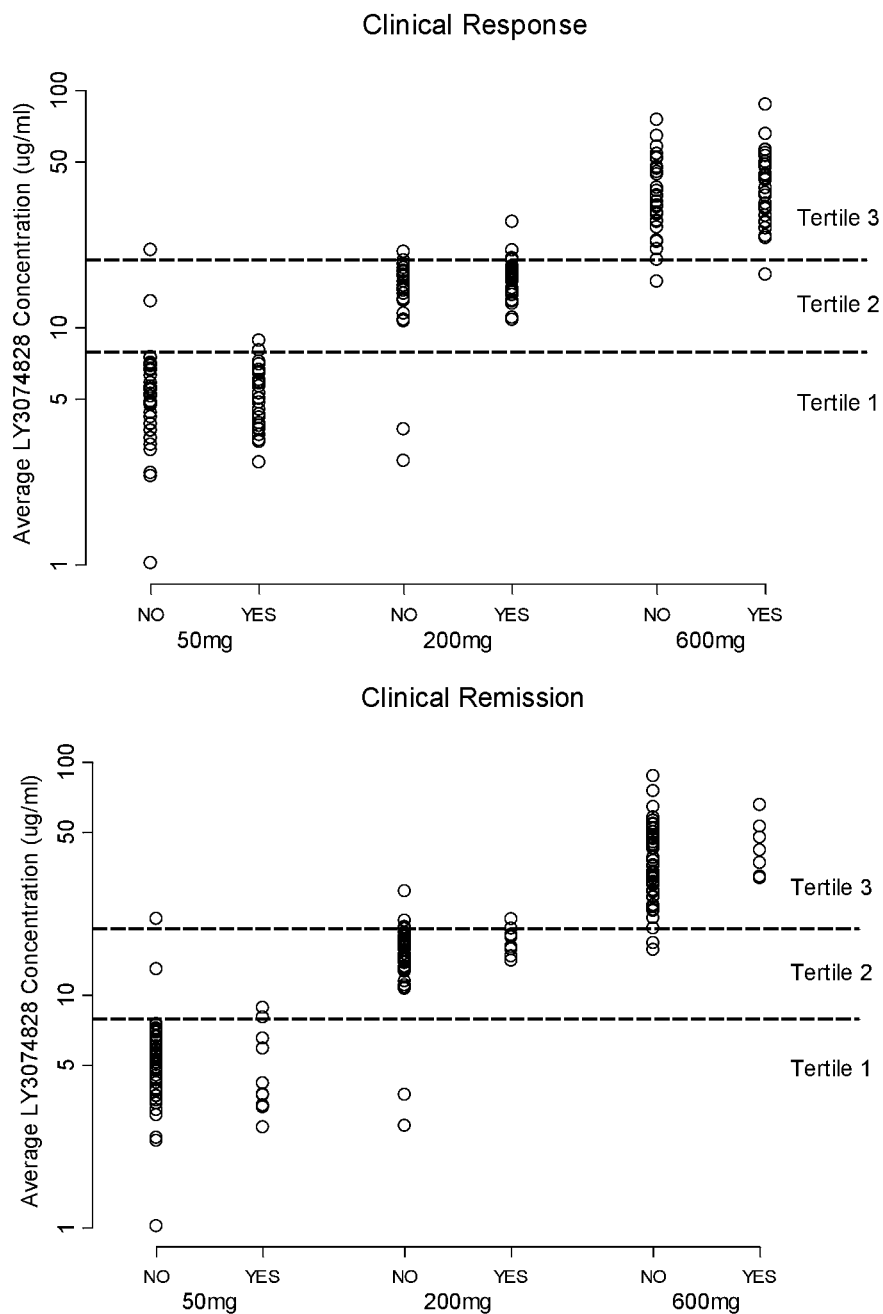

Note: Areas labeled Tertile 1, 2, and 3 are the tertiles of the model-estimated average concentrations for all patients who received LY3074828 (mirikizumab). The overall average doses in the 50-mg and 200-mg groups during induction were 100 mg and 250 mg, respectively.

Figure 3: Model-estimated average concentration of mirikizumab during induction in patients based on clinical response (upper panel) or clinical remission (lower panel) status

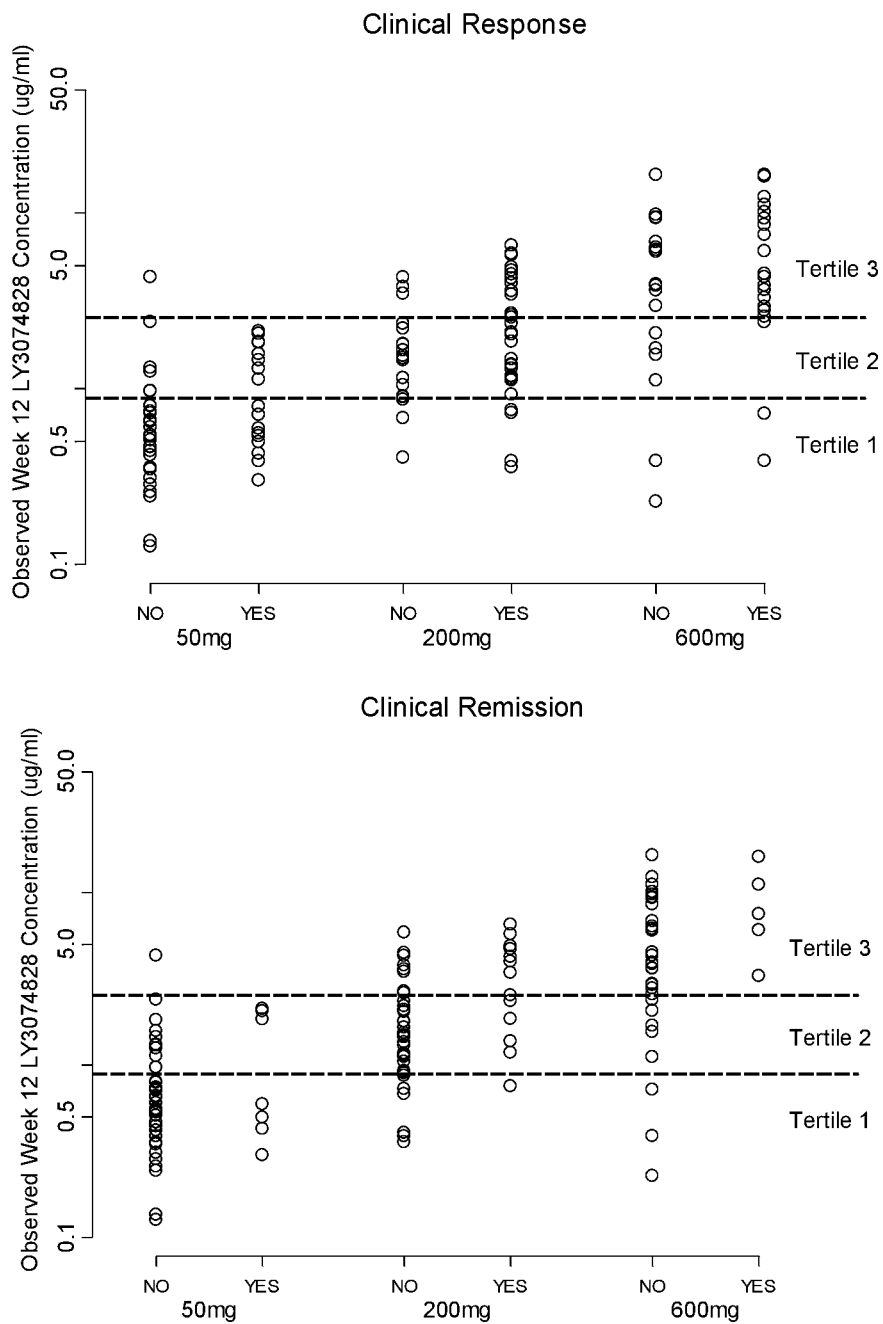

Note: Areas labeled Tertile 1, 2, and 3 are the tertiles of the observed Week 12 concentrations for all patients who received LY3074828 (mirikizumab). The overall average doses in the 50-mg and 200-mg groups during induction were 100 mg and 250 mg, respectively.

Figure 4: Observed Week 12 concentration of mirikizumab during induction in patients based on clinical response (upper panel) or clinical remission (lower panel) status

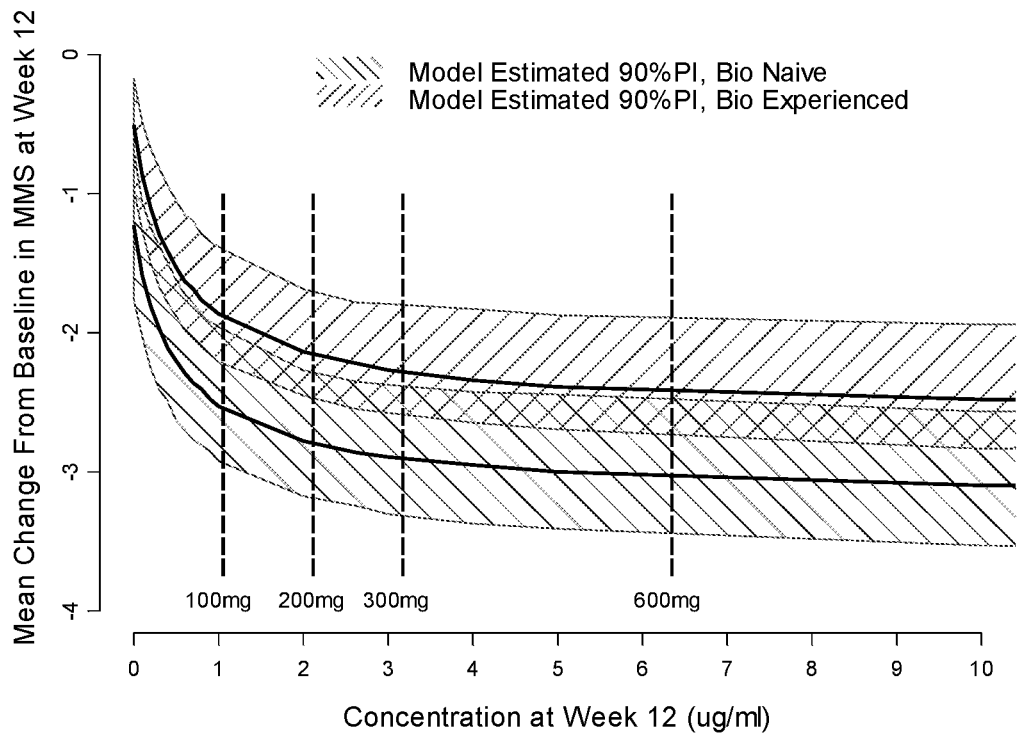

Abbreviations: PI = projection interval; Bio Naive = biologic-naive; Bio Experienced = biologic-experienced.

Note: Projection intervals are based on simulation of 500 replicated trials with an N = 500 each for biologic-naive and biologic-experienced patients. Vertical dashed lines represent the median expected Week 12 concentrations for fixed IV doses administered Q4W.

Figure 5: Model-simulated change in modified Mayo score at Week 12 versus Week 12 concentration of mirikizumab

METHODS OF TREATING ULCERATIVE COLITIS WITH AN ANTI-IL-23p19 ANTIBODY

The present invention relates to methods of treating ulcerative colitis. Ulcerative colitis (UC) is a chronic disease of unknown cause that is characterized by inflammation in the colon. Patients have intermittent disease flares interspersed with periods of remission; the primary symptoms are blood in the stool, diarrhea, and abdominal pain, which reduce overall quality of life. Many patients with UC experience a severe clinical course: approximately 30% require colectomy within 10 years of diagnosis (Ordás et al., Lancet, Vol. 380, No. 9853, pp1606-1619, 2012). The treatment goal in UC is the induction and maintenance of remission (including steroid-free remission). Conventional medications used for treatment of UC include 5-aminosalicylic acid (5-ASA), steroids, and immunosuppressive drugs such as azathioprine (AZA) and 6-mercaptopurine (6-MP). However, as many as 40% of patients with UC do not respond or maintain a response to conventional medications and require secondary drug treatment or colectomy (Burger D et al., Gastroenterology, Vol. 140, No. 6, pp1827-1837, 2011). As a result, various biologics that target specific immunological pathways have been studied as potential therapeutics for UC. Anti-tumor necrosis factor-α (anti-TNF-α) monoclonal antibodies and more recently vedolizumab, an integrin receptor antagonist, have been approved by the Food and Drug Administration and by the European Medicines Agency.

Interleukin-23 (IL-23), a member of the interleukin-12 (IL-12) family of cytokines, is a heterodimeric protein composed of two subunits: the p40 subunit, which is shared by IL-12, and the p19 subunit, which is specific to IL-23. IL-23 is produced by antigen-presenting cells, such as dendritic cells and macrophages and is critically involved in the maintenance and amplification of T helper 17 (Th17) cells. Stimulation of these cells with IL-23 induces a unique inflammatory signature that includes interleukin-17A, interleukin-17F, interleukin-6, granulocyte-macrophage-colony stimulating factor, tumor necrosis factor α, chemokine ligand 20, chemokine ligand 22, and IL-23 receptor. In addition to Th17 cells, many innate immune cells respond to IL-23 and are important both in resistance to infection and in mediating pathology in many autoimmune/inflammatory diseases including UC and Crohn's Disease (CD). Treatment of a number of conditions with IL-23 targeted therapy is being pursued by several companies. The first such biologic to demonstrate clinical benefit in autoimmune disease was ustekinumab, which is a Food and Drug Administration—approved monoclonal antibody for the treatment of psoriasis, psoriatic arthritis and CD. Ustekinumab binds the common p40 subunit of IL-12 and IL-23; therefore, it targets both cytokines, rather than IL-23 specifically. Blockade of the IL-12 pathway may prevent Th1 cell—induced interferon blockade of Th17 cell development, thus potentially limiting the clinical activity of p40 targeting antibodies. Agents specifically targeting the IL-23 p19 subunit have demonstrated clinical activity in psoriasis and CD (Kopp T et al., Nature, Volume 521, No. 7551, pages 222-226, 2015; Sands B E et al., Journal of Crohn's and Colitis, Volume 9, Issue Supplement 1, ppS15-S16, 2015).

The IL-23/Th17 pathway is believed to have a role in UC (El-Bassat H et al, Journal of Molecular Biomarkers & Diagnosis, Vol. 5, No. 5, 100191, 2014). Nevertheless, clinical evaluation of an IL-23 targeted therapy in UC has yet to occur and there remains a need for treatment options for ulcerative colitis that lead to favourable outcomes for patients, for example, in terms of efficacy, safety and/or tolerability of the treatment. In particular, there remains a need for treatment options in the form of dosage regimen that provide optimal efficacy.

Accordingly, in a first aspect of the present invention, there is a provided a method of treating ulcerative colitis (UC) comprising administering to a patient in need thereof an effective amount of an anti-IL-23p19 antibody, said method comprising:

a) administering at least one induction dose of the anti-IL-23p19 antibody to the patient, wherein the induction dose comprises 50 mg to 1200 mg of the antibody; and b) administering at least one maintenance dose(s) of the anti-IL-23p19 antibody to the patient after the last induction dose is administered, wherein the maintenance dose comprises 150 to 400 mg of the anti-IL-23p19 antibody.

The method of the present invention comprises administration of at least one induction dose of an anti-IL-23p19 antibody to a patient in need thereof in an induction period to induce a desired therapeutic effect, the desired therapeutic effect being clinical remission, clinical response, endoscopic remission, endoscopic healing and/or symptomatic remission. If the patient achieves a desired therapeutic effect at the end of the induction period, he/she is subsequently administered at least one maintenance dose to maintain at least one of the therapeutic effect(s) obtained during the induction period, the therapeutic effect(s) being clinical remission, clinical response, endoscopic remission, endoscopic healing and/or symptomatic remission.

There is no minimum or maximum duration of the induction period but it is typically 4, 8 or 12 weeks in duration, with the end of induction period being an end-of-induction assessment typically occurring 4 or 8 weeks after the last induction dose has been administered. For instance, an induction period of 4 weeks may comprise administration of an induction dose at Week 0 and an end-of-induction assessment at Week 4. An induction period of 8 weeks may comprise administration of induction doses at Week 0 and Week 4 and an end-of-induction assessment at Week 8. An induction period of 12 weeks may comprise administration of induction doses at Week 0, Week 4 and Week 8 and an end-of-induction assessment at Week 12.

In an embodiment of the present invention, the ulcerative colitis is moderate to severe ulcerative colitis.

In a further embodiment of the method of the present invention, the patient is biologic-naïve. In an alternative embodiment of the method of the present invention, the patient is biologic-experienced. In a further alternative embodiment of the method of the present invention, the patient is biologic-failed or conventional-failed.

In a still further embodiment of the method of the present invention, the at least one induction dose comprises 200 mg to 1000 mg of the anti-IL-23p19 antibody.

In a still further embodiment of the method of the present invention, the at least one induction dose comprises 200 mg to 600 mg of the anti-IL-23p19 antibody.

In a still further embodiment of the method of the present invention, the at least one induction dose comprises 50 mg, 100 mg, 200 mg, 250 mg, 300 mg or 600 mg of the anti-IL-23p19 antibody.

In a preferred embodiment of the method of the present invention, the at least one induction dose comprises 300 mg of the anti-IL-23p19 antibody.

In a still further embodiment of the method of the present invention, one, two or three induction doses are administered to the patient.

In a still further embodiment of the method of the present invention, two or three induction doses are administered at 4 week intervals.

In a preferred embodiment of the method of the present invention, three induction doses are administered at 4 week intervals.

In a still further embodiment of the method of the present invention, the at least one induction dose is administered by intravenous infusion.

In a still further embodiment of the method of the present invention, if the patient has not achieved clinical response 4-12 weeks after the last induction dose is administered, one, two or three extended induction dose(s) of the anti-IL-23p19 antibody are administered to the patient, wherein the at least one maintenance dose(s) of the anti-IL-23p19 antibody is administered to the patient if the patient has achieved clinical response 4-12 weeks after the last extended induction dose is administered, and wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1.

This embodiment of the method of the present invention comprises administration of one, two or three further induction doses—termed "extended induction dose" to distinguish it from the initial induction dose—if the patient does not achieve clinical response at the end of the initial induction period. The dose and dosing intervals during the extended induction period are typically the same as dose and dosing intervals during the initial induction period but may be changed if the attending health care professional has reason to believe that the patient may benefit from changes such as an increased dose of the anti-IL-23p19 antibody or more frequent dosing. If the patient achieves clinical response at the end of the extended induction period, at least one maintenance dose of the anti-IL-23p19 antibody is administered to maintain clinical response or other desired therapeutic effect(s) such as clinical remission, endoscopic remission, endoscopic healing and/or symptomatic remission.

The first maintenance dose is administered 4-12 weeks after the last extended induction dose is administered to the patient. The 4-12 week period accommodates variation in the period between the administration of last extended induction dose and the end of extended-induction assessment. The variation may arise from variation in the dosing frequency in the extended induction period. For instance, the dosing frequency in the extended induction period is every 4 weeks and the end-of-extended induction assessment occurs 4 weeks after the last extended induction dose is administered. If the patient has achieved clinical response, the first maintenance dose may be administered at the end-of-induction assessment visit (that is, 4 weeks after administration of the last extended induction dose) or may be administered at a subsequent visit scheduled to occur shortly thereafter. Alternatively, the dosing frequency in the extended induction period is every 8 weeks and the end-of-extended induction assessment occurs 8 weeks after the last extended induction dose is administered. If the patient has achieved clinical response, the first maintenance dose may be administered at the end-of-induction assessment visit (that is, 8 weeks after administration of the last extended induction dose) or may be administered at a subsequent visit scheduled to occur shortly thereafter.

In a still further embodiment of the method of the present invention, the one, two or three extended induction dose(s) are administered to the patient if the patient has not achieved clinical response 4 weeks after the last induction dose is administered.

In a still further embodiment of the method of the present invention, two or three extended induction doses are administered at 4 week intervals.

In a preferred embodiment of the method of the present invention, three extended induction doses are administered at 4 week intervals. In a still further embodiment of the method of the present invention, one, two or three extended induction dose(s) comprise 50 mg, 100 mg, 200 mg, 250 mg, 300 mg or 600 mg of the anti-IL-23p19 antibody.

In a preferred embodiment of the method of the present invention, the one, two or three extended induction dose(s) comprise 300 mg of the anti-IL-23p19 antibody. In a still further embodiment of the method of the present invention, the one, two or three extended induction dose(s) are administered by intravenous infusion.

In a still further embodiment of the method of the present invention, the at least one maintenance dose comprises 150 mg, 200 mg, 250 mg or 300 mg of the anti-IL-23p19 antibody.

In a preferred embodiment of the method of the present invention, the at least one maintenance dose comprises 200 mg of the anti-IL-23p19 antibody.

In a still further embodiment of the method of the present invention, multiple maintenance doses are administered to a patient and wherein the first maintenance dose is administered 2 to 8 weeks after the last induction dose or last extended induction dose is administered.

Preferably, the first maintenance dose is administered 4 to 6 weeks after the last induction dose or last extended induction dose is administered.

Alternatively preferably, the first maintenance dose is administered 2 weeks, 3 weeks, 4 weeks, 5 weeks, 6 weeks, 7 weeks, or 8 weeks after the last induction dose or last extended induction dose is administered.

Still further preferably, the first maintenance dose is administered 4 weeks after the last induction dose or last extended induction dose is administered.

In a still further embodiment of the method of the present invention, subsequent maintenance dose(s) are administered at 4, 8 or 12 week interval(s) after administration of the first maintenance dose.

Preferably, subsequent maintenance dose(s) are administered at 4 week interval(s).

Alternatively, preferably subsequent maintenance dose(s) are administered at 8 week interval(s).

Alternatively preferably, subsequent further maintenance dose(s) are administered at 12 week interval(s).

In a still further embodiment of the method of the present invention, the maintenance dose(s) are administered by subcutaneous injection.

In a still further embodiment of the method of the present invention, if the patient develops a loss of response during the maintenance period, one, two or three rescue dose(s) of the anti-IL-23p19 antibody are administered to the patient, wherein one or more further maintenance dose(s) of the anti-IL-23p19 antibody are administered to the patient if the patient achieves clinical response 4-12 weeks after the last rescue dose is administered, wherein loss of response is defined as: (a) ≥2-point increase from baseline in the combined stool frequency (SF) and rectal bleeding (RB) scores (b) combined SF and RB score of ≥4, on 2 consecutive visits ≥7 days apart with confirmation of negative *Clostridium*

*difficile* testing and (c) endoscopic subscore (ES) of 2 or 3, and wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1.

This embodiment of the present invention comprises administration of one, two or three rescue doses of the anti-IL-23p19 antibody if the patient develops a loss of response during the maintenance period. The rescue dose is a dose of an anti-IL-23p19 antibody administered to a patient in order to re-induce/re-achieve the therapeutic effect achieved at the end of the induction period, the therapeutic effect being clinical remission, clinical response, endoscopic remission, endoscopic healing and/or symptomatic remission. The rescue dose and dosing intervals during the rescue dosing period are typically the same as dose and dosing intervals during the initial induction period but may be changed if the attending health care professional has reason to believe that the patient may benefit from changes such as an increased dose of the anti-IL-23p19 antibody or more frequent dosing.

If the patient achieves clinical response at the end of the rescue dosing period, maintenance therapy is restarted and one or more further maintenance dose(s) of the anti-IL-23p19 antibody is administered to the patient. These maintenance doses are termed "further maintenance dose(s)" to identify them as doses the maintenance doses that are administered when maintenance therapy is restarted. The further maintenance dose is a dose of an anti-IL-23p19 antibody administered to a patient to maintain or continue a clinical response or other desired therapeutic effect(s) such as clinical remission, endoscopic remission, endoscopic healing and/or symptomatic remission that is achieved after administration of rescue dose(s) during the rescue period. The further maintenance dose(s) and dosing intervals during the restarted maintenance therapy are typically the same as maintenance dose and dosing intervals during the initial maintenance period but may be changed if the attending health care professional has reason to believe that the patient may benefit from changes such as an increased dose of the anti-IL-23p19 antibody or more frequent dosing.

The first further maintenance dose is administered 4-12 weeks after the last rescue dose is administered to the patient. The 4-12 week period accommodates variation in the period between the administration of last rescue dose and the end-of-rescue assessment. The variation may arise from variation in the dosing frequency in the rescue period. For instance, the dosing frequency in the rescue period is every 4 weeks and the end-of-extended induction assessment occurs 4 weeks after the last extended induction dose is administered. If the patient has achieved clinical response, the first further maintenance dose may be administered at the end-of-rescue assessment visit (that is, 4 weeks after administration of the last rescue dose) or may be administered at a subsequent visit scheduled to occur shortly thereafter. Alternatively, the dosing frequency in the rescue period is every 8 weeks and the end-of-rescue assessment occurs 8 weeks after the last rescue dose is administered. If the patient has achieved clinical response, the first further maintenance dose may be administered at the end-of-induction assessment visit (that is, 8 weeks after administration of the last rescue dose) or may be administered at a subsequent visit scheduled to occur shortly thereafter.

In a still further embodiment of the method of the present invention, two or three rescue doses are administered at 4 week intervals.

In a preferred embodiment of the method of the present invention three rescue doses are administered at 4 week intervals.

In a still further embodiment of the method of the present invention the one, two or three rescue dose(s) comprise 50 mg, 100 mg, 200 mg, 250 mg, 300 mg or 600 mg of the anti-IL-23p19 antibody.

Preferably, the one, two or three rescue dose(s) comprise 300 mg of the anti-IL-23p19 antibody.

In a still further embodiment of the method of the present invention the one, two or three rescue dose(s) are administered by intravenous infusion.

In a still further embodiment of the method of the present invention, the one or more further maintenance dose(s) comprise 150 mg, 200 mg, 250 mg or 300 mg of the anti-IL-23p19 antibody.

In a preferred embodiment of the method of the present invention, the one or more further maintenance dose(s) comprise 200 mg of the anti-IL-23p19 antibody. In a still further embodiment of the method of the present invention, multiple further maintenance doses are administered to a patient and wherein the first further maintenance dose is administered 2 weeks, 3 weeks, 4 weeks, 5 weeks, 6 weeks, 7 weeks, or 8 weeks after the last rescue dose is administered.

Preferably, the first further maintenance dose is administered 4 weeks after the last rescue dose is administered.

In a still further embodiment of the method of the present invention, subsequent further maintenance dose(s) are administered at 4, 8 or 12 week interval(s) after administration of the first further maintenance dose.

Preferably, subsequent further maintenance dose(s) are administered at 4 week interval(s).

Alternatively preferably, subsequent further maintenance dose(s) are administered at 8 week interval(s).

Further alternatively preferably, subsequent further maintenance dose(s) are administered at 12 week interval(s).

In a still further embodiment of the method of the present invention, the further maintenance dose(s) are administered by subcutaneous injection.

In a still further embodiment of the method of the present invention, the anti-IL-23p19 antibody is mirikizumab, guselkumab, tildrakizumab, risankizumab or brazikumab.

In a preferred embodiment of the method of the present invention, the anti-IL-23p19 antibody is mirikizumab.

In a still further embodiment of the method of the present invention, the method comprises:
a) administering three induction doses of mirikizumab to the patient by intravenous infusion at 4 week intervals, wherein each induction dose comprises 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered and wherein each maintenance dose comprises 200 mg of mirikizumab.

In a preferred embodiment of the method of the present invention, the first maintenance dose is administered 4-6 weeks after the last induction dose is administered.

In a further preferred embodiment of the method of the present invention, subsequent maintenance dose(s) of mirikizumab are administered at 4 week intervals after administration of the first maintenance dose.

In an alternative preferred embodiment of the method of the present invention, subsequent maintenance dose(s) of mirikizumab are administered at 12 week intervals after administration of the first maintenance dose.

In a still further embodiment of the method of the present invention, the method comprises:
a) administering three induction doses of mirikizumab to the patient by intravenous infusion at 4 week intervals, wherein, if the patient has not achieved clinical response 4 weeks after the last induction dose is administered, three extended induction doses of mirikizumab are administered to the patient, and, wherein each induction dose and each extended induction dose comprise 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered and wherein each maintenance dose comprises 200 mg of mirikizumab.

In a preferred embodiment of the method of the present invention, the first maintenance dose is administered 4-6 weeks after the last induction dose or last extended induction dose is administered.

In a further preferred embodiment of the method of the present invention, subsequent maintenance doses of mirikizumab are administered at 4 week intervals after administration of the first maintenance dose.

In an alternative preferred embodiment of the method of the present invention, subsequent maintenance doses of mirikizumab are administered at 12 week intervals after administration of the first maintenance dose.

In a still further embodiment of the method of the present invention, the method comprises:
a) administering three induction doses of mirikizumab to the patient by intravenous infusion at 4 week intervals, wherein each induction dose comprises 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered,
wherein if the patient develops a loss of response during the maintenance period, three rescue doses of mirikizumab are administered to the patient at 4 week intervals, wherein each rescue dose comprises 300 mg of mirikizumab,
wherein further maintenance doses of mirikizumab are administered to the patient if the patient achieves clinical response 4 weeks after the last rescue dose is administered, wherein the first further maintenance dose is administered 2-8 weeks after the last rescue dose is administered,
wherein loss of response is defined as: (a) ≥2-point increase from baseline in the combined stool frequency (SF) and rectal bleeding (RB) scores (b) combined SF and RB score of ≥4, on 2 consecutive visits ≥7 days apart with confirmation of negative *Clostridium difficile* testing and (c) endoscopic subscore (ES) of 2 or 3,
wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1; and
wherein each maintenance dose comprises 200 mg of mirikizumab.

In a preferred embodiment of the method of the present invention, the first maintenance dose is administered 4-6 weeks after the last induction dose is administered and the first further maintenance dose is administered 4-6 weeks after the last rescue dose is administered.

In a further preferred embodiment of the method of the present invention, subsequent maintenance dose(s) of mirikizumab are administered at 4 week intervals after administration of the first maintenance dose and subsequent further maintenance dose(s) of mirikizumab are administered at 4 week intervals after administration of the first further maintenance dose.

In an alternative preferred embodiment of the method of the present invention, subsequent maintenance dose(s) of mirikizumab are administered at 12 week intervals after administration of the first maintenance dose and subsequent further maintenance dose(s) of mirikizumab are administered at 12 week intervals after administration of the first further maintenance dose.

In a still further embodiment of the method of the present invention, the method comprises:
a) administering three induction doses of mirikizumab to the patient by intravenous infusion at 4 week intervals, wherein, if the patient has not achieved clinical response 4 weeks after the last induction dose is administered, three extended induction doses of mirikizumab are administered to the patient, and, wherein each induction dose and each extended induction dose comprise 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered,
wherein if the patient develops a loss of response during the maintenance period, three rescue doses of mirikizumab are administered to the patient at 4 week intervals, wherein each rescue dose comprises 300 mg of mirikizumab,
wherein further maintenance dose(s) of mirikizumab are administered to the patient if the patient achieves clinical response 4 weeks after the last rescue dose is administered, wherein the first further maintenance dose(s) is administered 2-8 weeks after the last rescue dose is administered,
wherein loss of response is defined as: (a) ≥2-point increase from baseline in the combined stool frequency (SF) and rectal bleeding (RB) scores (b) combined SF and RB score of ≥4, on 2 consecutive visits ≥7 days apart with confirmation of negative *Clostridium. difficile* testing and (c) endoscopic subscore (ES) of 2 or 3,
wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1,
and wherein each maintenance dose and each further maintenance dose comprises 200 mg of mirikizumab.

In a preferred embodiment of the method of the present invention, the first maintenance dose is administered 4-6 weeks after the last induction dose or last extended induction dose is administered and the first further maintenance dose is administered 4-6 weeks after the last rescue dose is administered.

In a further preferred embodiment of the method of the present invention, subsequent maintenance dose(s) of mirikizumab are administered at 4 week intervals after administration of the first maintenance dose and subsequent further maintenance dose(s) of mirikizumab are administered at 4 week intervals after administration of the first further maintenance dose.

In an alternative preferred embodiment of the method of the present invention, subsequent maintenance doses of mirikizumab are administered at 12 week intervals after administration of the first maintenance dose and subsequent further maintenance doses of mirikizumab are administered at 12 week intervals after administration of the first further maintenance dose.

In a further aspect of the present invention, there is provided an anti-IL-23p19 antibody for use in the treatment of UC, wherein the treatment comprises:
a) administering at least one induction dose of the anti-IL-23p19 antibody to the patient, wherein the induction dose comprises 50 mg to 1200 mg of the antibody; and
b) administering at least one maintenance dose(s) of the anti-IL-23p19 antibody to the patient after the last induction dose is administered, wherein the maintenance dose comprises 150 to 400 mg of the anti-IL-23 p19 antibody.

In an embodiment of the present invention, the UC is moderate to severe ulcerative colitis.

In a further embodiment of the present invention, the patient is biologic-naïve. In an alternative embodiment of the present invention, the patient is biologic-experienced.

In a further alternative embodiment of the present invention, the patient is biologic-failed or conventional-failed.

In a still further embodiment of the present invention, the at least one induction dose comprises 200 mg to 1000 mg of the anti-IL-23p19 antibody.

In a still further embodiment of the present invention, the at least one induction dose comprises 200 mg to 600 mg of the anti-IL-23p19 antibody.

In a still further embodiment of the present invention, the at least one induction dose comprises 50 mg, 100 mg, 200 mg, 250 mg, 300 mg or 600 mg of the anti-IL-23p19 antibody.

In a preferred embodiment of the present invention, the at least one induction dose comprises 300 mg of the anti-IL-23p19 antibody.

In a still further embodiment of the present invention, one, two or three induction doses are administered to the patient.

In a still further embodiment of the present invention, two or three induction doses are administered at 4 week intervals.

In a preferred embodiment of the present invention, three induction doses are administered at 4 week intervals.

In a still further embodiment of the present invention, the at least one induction dose is administered by intravenous infusion.

In a still further embodiment of the present invention, if the patient has not achieved clinical response 4-12 weeks after the last induction dose is administered, one, two or three extended induction dose(s) of the anti-IL-23p19 antibody are administered to the patient, wherein the at least one maintenance dose(s) of the anti-IL-23p19 antibody is administered to the patient if the patient has achieved clinical response 4-12 weeks after the last extended induction dose is administered, and wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1.

In a still further embodiment of the present invention, the one, two or three extended induction dose(s) are administered to the patient if the patient has not achieved clinical response 4 weeks after the last induction dose is administered.

In a still further embodiment of the present invention, two or three extended induction doses are administered at 4 week intervals.

In a preferred embodiment of the present invention, three extended induction doses are administered at 4 week intervals.

In a still further embodiment of the present invention, one, two or three extended induction dose(s) comprise 50 mg, 100 mg, 200 mg, 250 mg, 300 mg or 600 mg of the anti-IL-23p19 antibody.

In a preferred embodiment of the present invention, the one, two or three extended induction dose(s) comprise 300 mg of the anti-IL-23p19 antibody.

In a still further embodiment of the present invention, the one, two or three extended induction dose(s) are administered by intravenous infusion.

In a still further embodiment of the present invention, the at least one maintenance dose comprises 150 mg, 200 mg, 250 mg or 300 mg of the anti-IL-23p19 antibody.

In a preferred embodiment of the present invention, the at least one maintenance dose comprises 200 mg of the anti-IL-23p19 antibody.

In a still further embodiment of the present invention, multiple maintenance doses are administered to a patient and wherein the first maintenance dose is administered 2 to 8 weeks after the last induction dose or last extended induction dose is administered.

Preferably, the first maintenance dose is administered 4 to 6 weeks after the last induction dose or last extended induction dose is administered.

Alternatively preferably, the first maintenance dose is administered 2 weeks, 3 weeks, 4 weeks, 5 weeks, 6 weeks, 7 weeks, or 8 weeks after the last induction dose or last extended induction dose is administered.

Further preferably, the first maintenance dose is administered 4 weeks after the last induction dose or last extended induction dose is administered.

In a still further embodiment of the present invention, subsequent maintenance dose(s) are administered at 4, 8 or 12 week interval(s) after administration of the first maintenance dose.

Preferably, subsequent maintenance dose(s) are administered at 4 week interval(s).

Alternatively preferably, subsequent further maintenance dose(s) are administered at 8 week interval(s).

Further alternatively preferably, subsequent maintenance dose(s) are administered at 12 week interval(s).

In a still further embodiment of the present invention, the maintenance dose(s) are administered by subcutaneous injection.

In a still further embodiment of the present invention, if the patient develops a loss of response during the maintenance period, one, two or three rescue dose(s) of the anti-IL-23p19 antibody are administered to the patient, wherein one or more further maintenance dose(s) of the anti-IL-23p19 antibody are administered to the patient if the patient achieves clinical response 4-12 weeks after the last rescue dose is administered, wherein loss of response is defined as: (a) ≥2-point increase from baseline in the combined stool frequency (SF) and rectal bleeding (RB) scores (b) combined SF and RB score of ≥4, on 2 consecutive visits ≥7 days apart with confirmation of negative *Clostridium. difficile* testing and (c) endoscopic subscore (ES) of 2 or 3, and wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1.

In a still further embodiment of the present invention, two or three rescue doses are administered at 4 week intervals.

In a preferred embodiment of the present invention, three rescue doses are administered at 4 week intervals.

In a still further embodiment of the present invention, the one, two or three rescue dose(s) comprise 50 mg, 100 mg, 200 mg, 250 mg, 300 mg or 600 mg of the anti-IL-23p19 antibody.

In a preferred embodiment of the present invention, the one, two or three rescue dose(s) comprise 300 mg of the anti-IL-23p19 antibody.

In a still further embodiment of the present invention, the one, two or three rescue dose(s) are administered by intravenous infusion.

In a still further embodiment of the present invention, the one or more further maintenance dose(s) comprise 150 mg, 200 mg, 250 mg or 300 mg of the anti-IL-23p19 antibody.

In a preferred embodiment of the present invention, the one or more further maintenance dose(s) comprise 200 mg of the anti-IL-23p19 antibody.

In a preferred embodiment of the present invention, multiple further maintenance doses are administered to a patient and wherein the first further maintenance dose is administered 2 weeks, 3 weeks, 4 weeks, 5 weeks, 6 weeks, 7 weeks, or 8 weeks after the last rescue dose is administered.

Preferably, the first further maintenance dose is administered 4 weeks after the last rescue dose is administered.

In a still further embodiment of the present invention, subsequent further maintenance dose(s) are administered at 4, 8 or 12 week interval(s) after administration of the first further maintenance dose.

Preferably, the subsequent further maintenance dose(s) are administered at 4 week interval(s).

Alternatively preferably, subsequent further maintenance dose(s) are administered at 8 week interval(s).

Further alternatively preferably, subsequent further maintenance dose(s) are administered at 12 week interval(s).

In a still further embodiment of the present invention, the further maintenance dose(s) are administered by subcutaneous injection.

In a still further embodiment of the present invention, the anti-IL-23p19 antibody is mirikizumab, guselkumab, tildrakizumab, risankizumab or brazikumab.

In a preferred embodiment of the present invention, the anti-IL-23p19 antibody is mirikizumab.

In a still further embodiment of the present invention, the treatment comprises:
a) administering three induction doses of mirikizumab to the patient by intravenous infusion at 4 week intervals, wherein each induction dose comprises 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered and wherein each maintenance dose comprises 200 mg of mirikizumab.

In a preferred embodiment of the present invention, the first maintenance dose is administered 4-6 weeks after the last induction dose is administered.

In a further preferred embodiment of the present invention, the subsequent maintenance dose(s) of mirikizumab are administered at 4 week intervals after administration of the first maintenance dose.

In an alternative preferred embodiment of the present invention, the further maintenance dose(s) of mirikizumab are administered at 12 week intervals after administration of the first maintenance dose.

In a still further embodiment of the present invention, the treatment comprises:
a) administering three induction doses of mirikizumab to the patient by intravenous infusion at 4 week intervals, wherein, if the patient has not achieved clinical response 4 weeks after the last induction dose is administered, three extended induction doses of mirikizumab are administered to the patient, wherein each induction dose and each extended induction dose comprises 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered and wherein each maintenance dose comprises 200 mg of mirikizumab.

In a preferred embodiment of the present invention, the first maintenance dose is administered 4-6 weeks after the last induction dose or last extended induction dose is administered.

In a further preferred embodiment of the present invention, subsequent maintenance dose(s) of mirikizumab are administered at 4 week intervals after administration of the first maintenance dose.

In an alternative preferred embodiment of the present invention, subsequent maintenance dose(s) of mirikizumab are administered at 12 week intervals after administration of the first maintenance dose.

In a still further embodiment of the present invention, the treatment comprises:
a) administering three induction doses of mirikizumab to the patient by intravenous infusion at 4 week intervals, wherein each induction dose comprises 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered,
wherein if the patient develops a loss of response during the maintenance period, three rescue doses of mirikizumab are administered to the patient at 4 week intervals,
wherein each rescue dose comprises 300 mg of mirikizumab,
wherein further maintenance doses of mirikizumab are administered to the patient if the patient achieves clinical response 4 weeks after the last rescue dose is administered, wherein the first further maintenance dose is administered 2-8 weeks after the last rescue dose is administered,
wherein loss of response is defined as: (a) ≥2-point increase from baseline in the combined stool frequency (SF) and rectal bleeding (RB) scores (b) combined SF and RB score of ≥4, on 2 consecutive visits ≥7 days apart with confirmation of negative *Clostridium difficile* testing and (c) endoscopic subscore (ES) of 2 or 3,
wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1,
and wherein each maintenance dose and each further maintenance dose comprises 200 mg of mirikizumab.

In a preferred embodiment of the present invention, the first maintenance dose is administered 4-6 weeks after the last induction dose is administered and the first further maintenance dose is administered 4-6 weeks after the last rescue dose is administered.

In a further preferred embodiment of the present invention, subsequent maintenance dose(s) of mirikizumab are administered at 4 week intervals after administration of the first maintenance dose and subsequent further maintenance dose(s) of mirikizumab are administered at 4 week intervals after administration of the first further maintenance dose.

In an alternative preferred embodiment of the present invention, subsequent maintenance dose(s) of mirikizumab are administered at 12 week intervals after administration of the first maintenance dose and subsequent further maintenance dose(s) of mirikizumab are administered at 12 week intervals after administration of the first further maintenance dose.

In a still further embodiment of the present invention, the treatment comprises:
a) administering three induction doses of mirikizumab to the patient by intravenous infusion at 4 week intervals, wherein, if the patient has not achieved clinical response 4 weeks after the last induction dose is administered, three extended induction doses of mirikizumab are administered to the patient, wherein each induction dose and each extended induction dose comprises 300 mg of mirikizumab,
wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1, and
b) administering maintenance doses of mirikizumab to the patient by subcutaneous injection at 4 week or 12 week intervals, wherein the first maintenance dose is administered 2-8 weeks after the last induction dose is administered,
wherein if the patient develops a loss of response during the maintenance period, three rescue doses of mirikizumab are administered to the patient at 4 week intervals, wherein each rescue dose comprises 300 mg of mirikizumab,
wherein further maintenance doses of mirikizumab are administered to the patient if the patient achieves clinical response 4 weeks after the last rescue dose is administered, wherein the first further maintenance dose is administered 2-8 weeks after the last rescue dose is administered,
wherein loss of response is defined as: (a) ≥2-point increase from baseline in the combined stool frequency (SF) and rectal bleeding (RB) scores (b) combined SF and RB score of ≥4, on 2 consecutive visits ≥7 days apart with confirmation of negative *Clostridium difficile* testing and (c) endoscopic subscore (ES) of 2 or 3,
wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1,
and wherein each maintenance dose and each further maintenance dose comprises 200 mg of mirikizumab.

In a preferred embodiment of the present invention, the first maintenance dose is administered 4-6 weeks after the last induction dose or last extended induction dose is administered and the first further maintenance is administered 4-6 weeks after the last rescue dose is administered.

In a further preferred embodiment of the present invention, subsequent maintenance dose(s) of mirikizumab are administered at 4 week intervals after administration of the first maintenance dose and subsequent further maintenance dose(s) of mirikizumab are administered at 4 week intervals after administration of the first further maintenance dose.

In an alternative preferred embodiment of the present invention, subsequent maintenance dose(s) of mirikizumab are administered at 12 week intervals after administration of the first maintenance dose and subsequent further maintenance dose(s) of mirikizumab are administered at 12 week intervals after administration of the first further maintenance dose.

In a further aspect of the present invention, there is provided use of anti-IL-23p19 antibody in the manufacture of a medicament for use in the treatment of UC, wherein the treatment comprises:
a) administering at least one induction dose of the anti-IL-23p19 antibody to the patient, wherein the induction dose comprises 50 mg to 1200 mg of the antibody; and
b) administering at least one maintenance dose(s) of the anti-IL-23p19 antibody to the patient after the last induction dose is administered, wherein the maintenance dose comprises 150 to 400 mg of the anti-IL-23p19 antibody.

In an embodiment of the present invention, the UC is moderate to severe ulcerative colitis.

In a further embodiment of the present invention, the patient is biologic-naïve. In an alternative embodiment of the present invention, the patient is biologic-experienced. In a further alternative embodiment of the present invention, the patient is biologic-failed or conventional-failed.

In a still further embodiment of the present invention, the at least one induction dose comprises 200 mg to 1000 mg of the anti-IL-23p19 antibody.

In a still further embodiment of the present invention, the at least one induction dose comprises 200 mg to 600 mg of the anti-IL-23p19 antibody.

In a still further embodiment of the present invention, the at least one induction dose comprises 50 mg, 100 mg, 200 mg, 250 mg, 300 mg or 600 mg of the anti-IL-23p19 antibody.

In a preferred embodiment of the present invention, the at least one induction dose comprises 300 mg of the anti-IL-23p19 antibody.

In a still further embodiment of the present invention, one, two or three induction doses are administered to the patient.

In a still further embodiment of the present invention, two or three induction doses are administered at 4 week intervals.

In a preferred embodiment of the present invention, three induction doses are administered at 4 week intervals.

In a still further embodiment of the present invention, the at least one induction dose is administered by intravenous infusion.

In a still further embodiment of the present invention, if the patient has not achieved clinical response 4-12 weeks after the last induction dose is administered, one, two or three extended induction dose(s) of the anti-IL-23p19 antibody are administered to the patient, wherein the at least one maintenance dose(s) of the anti-IL-23p19 antibody is administered to the patient if the patient has achieved clinical response 4-12 weeks after the last extended induction dose is administered, and wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1.

In a still further embodiment of the present invention, the one, two or three extended induction dose(s) are administered to the patient if the patient has not achieved clinical response 4 weeks after the last induction dose is administered.

In a still further embodiment of the present invention, two or three extended induction doses are administered at 4 week intervals.

In a preferred embodiment of the present invention, three extended induction doses are administered at 4 week intervals.

In a still further embodiment of the present invention, one, two or three extended induction dose(s) comprise 50 mg, 100 mg, 200 mg, 250 mg, 300 mg or 600 mg of the anti-IL-23p19 antibody.

In a preferred embodiment of the present invention, the one, two or three extended induction dose(s) comprise 300 mg of the anti-IL-23p19 antibody.

In a still further embodiment of the present invention, the one, two or three extended induction dose(s) are administered by intravenous infusion.

In a still further embodiment of the present invention, the at least one maintenance dose comprises 150 mg, 200 mg, 250 mg or 300 mg of the anti-IL-23p19 antibody.

In a preferred embodiment of the present invention, the at least one maintenance dose comprises 200 mg of the anti-IL-23p19 antibody.

In a still further embodiment of the present invention, multiple maintenance doses are administered to a patient and wherein the first maintenance dose is administered 2 to 8 weeks after the last induction dose or last extended induction dose is administered.

Preferably, the first maintenance dose is administered 4 to 6 weeks after the last induction dose or last extended induction dose is administered.

Alternatively preferably, the first maintenance dose is administered 2 weeks, 3 weeks, 4 weeks, 5 weeks, 6 weeks, 7 weeks, or 8 weeks after the last induction dose or last extended induction dose is administered.

Further preferably, the first maintenance dose is administered 4 weeks after the last induction dose or last extended induction dose is administered.

In a still further embodiment of the present invention, subsequent maintenance dose(s) are administered at 4, 8 or 12 week interval(s) after administration of the first maintenance dose.

Preferably, subsequent maintenance dose(s) are administered at 4 week interval(s).

Alternatively preferably, subsequent further maintenance dose(s) are administered at 8 week interval(s).

Further alternatively preferably, subsequent maintenance dose(s) are administered at 12 week interval(s).

In a still further embodiment of the present invention, the maintenance dose(s) are administered by subcutaneous injection.

In a still further embodiment of the present invention, if the patient develops a loss of response during the maintenance period, one, two or three rescue dose(s) of the anti-IL-23p19 antibody are administered to the patient, wherein one or more further maintenance dose(s) of the anti-IL-23p19 antibody are administered to the patient if the patient achieves clinical response 4-12 weeks after the last rescue dose is administered, wherein loss of response is defined as: (a)≥2-point increase from baseline in the combined stool frequency (SF) and rectal bleeding (RB) scores (b) combined SF and RB score of ≥4, on 2 consecutive visits≥7 days apart with confirmation of negative *Clostridium. difficile* testing and (c) endoscopic subscore (ES) of 2 or 3, and wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1.

In a still further embodiment of the present invention, two or three rescue doses are administered at 4 week intervals.

In a preferred embodiment of the present invention, three rescue doses are administered at 4 week intervals.

In a still further embodiment of the present invention, the one, two or three rescue dose(s) comprise 50 mg, 100 mg, 200 mg, 250 mg, 300 mg or 600 mg of the anti-IL-23p19 antibody.

In a preferred embodiment of the present invention, the one, two or three rescue dose(s) comprise 300 mg of the anti-IL-23p19 antibody.

In a still further embodiment of the present invention, the one, two or three rescue dose(s) are administered by intravenous infusion.

In a still further embodiment of the present invention, the one or more further maintenance dose(s) comprise 150 mg, 200 mg, 250 mg or 300 mg of the anti-IL-23p19 antibody.

In a preferred embodiment of the present invention, the one or more further maintenance dose(s) comprises 200 mg of the anti-IL-23p19 antibody.

In a preferred embodiment of the present invention, multiple further maintenance doses are administered to a patient and wherein the first further maintenance dose is administered 2 weeks, 3 weeks, 4 weeks, 5 weeks, 6 weeks, 7 weeks, or 8 weeks after the last rescue dose is administered.

Preferably, the first further maintenance dose is administered 4 weeks after the last rescue dose is administered.

In a still further embodiment of the present invention, subsequent further maintenance dose(s) are administered at 4, 8 or 12 week interval(s) after administration of the first further maintenance dose.

Preferably, the subsequent further maintenance dose(s) are administered at 4 week interval(s).

Alternatively preferably, subsequent further maintenance dose(s) are administered at 8 week interval(s).

Further alternatively preferably, subsequent further maintenance dose(s) are administered at 12 week interval(s).

In a still further embodiment of the present invention, the further maintenance dose(s) are administered by subcutaneous injection.

In a still further embodiment of the present invention, the anti-IL-23p19 antibody is mirikizumab, guselkumab, tildrakizumab, risankizumab or brazikumab.

In a preferred embodiment of the present invention, the anti-IL-23p19 antibody is mirikizumab.

In a still further embodiment of the present invention, the treatment comprises:
a) administering three induction doses of mirikizumab to the patient by intravenous infusion at 4 week intervals, wherein each induction dose comprises 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered and wherein each maintenance dose comprises 200 mg of mirikizumab.

In a preferred embodiment of the present invention, the first maintenance dose is administered 4-6 weeks after the last induction dose is administered.

In a further preferred embodiment of the present invention, the subsequent maintenance dose(s) of mirikizumab are administered at 4 week intervals after administration of the first maintenance dose.

In an alternative preferred embodiment of the present invention, the further maintenance dose(s) of mirikizumab are administered at 12 week intervals after administration of the first maintenance dose.

In a still further embodiment of the present invention, the treatment comprises:
a) administering three induction doses of mirikizumab to the patient by intravenous infusion at 4 week intervals, wherein, if the patient has not achieved clinical response 4 weeks after the last induction dose is administered, three extended induction doses of mirikizumab are administered to the patient, wherein each induction dose and each extended induction dose comprises 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered and wherein each maintenance dose comprises 200 mg of mirikizumab.

In a preferred embodiment of the present invention, the first maintenance dose is administered 4-6 weeks after the last induction dose or last extended induction dose is administered.

In a further preferred embodiment of the present invention, subsequent maintenance dose(s) of mirikizumab are administered at 4 week intervals after administration of the first maintenance dose.

In an alternative preferred embodiment of the present invention, subsequent maintenance dose(s) of mirikizumab are administered at 12 week intervals after administration of the first maintenance dose.

In a still further embodiment of the present invention, the treatment comprises:
a) administering three induction doses of mirikizumab to the patient by intravenous infusion at 4 week intervals, wherein each induction dose comprises 300 mg of mirikizumab; and
b) administering maintenance doses of mirikizumab to the patient by subcutaneous injection at 4 week or 12 week intervals, wherein the first maintenance dose is administered 2-8 weeks after the last induction dose is administered,
wherein if the patient develops a loss of response during the maintenance period, three rescue doses of mirikizumab are administered to the patient at 4 week intervals,
wherein each rescue dose comprises 300 mg of mirikizumab, wherein further maintenance doses of mirikizumab are administered to the patient if the patient achieves clinical response 4 weeks after the last rescue dose is administered, wherein the first further maintenance dose is administered 2-8 weeks after the last rescue dose is administered,
wherein loss of response is defined as: (a) ≥2-point increase from baseline in the combined stool frequency (SF) and rectal bleeding (RB) scores (b) combined SF and RB score of ≥4, on 2 consecutive visits ≥7 days apart with confirmation of negative *Clostridium difficile* testing and (c) endoscopic subscore (ES) of 2 or 3,
wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1,
and wherein each maintenance dose and each further maintenance dose comprises 200 mg of mirikizumab.

In a preferred embodiment of the present invention, the first maintenance dose is administered 4-6 weeks after the last induction dose is administered and the first further maintenance dose is administered 4-6 weeks after the last rescue dose is administered.

In a further preferred embodiment of the present invention, subsequent maintenance dose(s) of mirikizumab are administered at 4 week intervals after administration of the first maintenance dose and subsequent further maintenance dose(s) of mirikizumab are administered at 4 week intervals after administration of the first further maintenance dose.

In an alternative preferred embodiment of the present invention, subsequent maintenance dose(s) of mirikizumab are administered at 12 week intervals after administration of the first maintenance dose and subsequent further maintenance dose(s) of mirikizumab are administered at 12 week intervals after administration of the first further maintenance dose.

In a still further embodiment of the present invention, the treatment comprises:
a) administering three induction doses of mirikizumab to the patient by intravenous infusion at 4 week intervals, wherein, if the patient has not achieved clinical response 4 weeks after the last induction dose is administered, three extended induction doses of mirikizumab are administered to the patient, wherein each induction dose and each extended induction dose comprises 300 mg of mirikizumab,
wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1, and
b) administering maintenance doses of mirikizumab to the patient by subcutaneous injection at 4 week or 12 week intervals, wherein the first maintenance dose is administered 2-8 weeks after the last induction dose is administered,
wherein if the patient develops a loss of response during the maintenance period, three rescue doses of mirikizumab are administered to the patient at 4 week intervals, wherein each rescue dose comprises 300 mg of mirikizumab, wherein further maintenance doses of mirikizumab are administered to the patient if the patient achieves clinical response 4 weeks after the last rescue dose is administered, wherein the first further maintenance dose is administered 2-8 weeks after the last rescue dose is administered, wherein loss of response is defined as: (a) ≥2-point increase from baseline in the combined stool frequency (SF) and rectal bleeding (RB) scores (b) combined SF and RB score of ≥4, on 2 consecutive visits ≥7 days apart with confirmation of negative *Clostridium difficile* testing and (c) endoscopic subscore (ES) of 2 or 3, wherein clinical response is defined as achieving a decrease in the 9 point Modified Mayo Score (MMS) subscore of ≥2 points and ≥30-35% from baseline, with either a decrease of rectal bleeding (RB) subscore of ≥1 or a RB subscore of 0 or 1, and wherein each maintenance dose and each further maintenance dose comprises 200 mg of mirikizumab.

In a preferred embodiment of the present invention, the first maintenance dose is administered 4-6 weeks after the last induction dose or last extended induction dose is administered and the first further maintenance dose is administered 4-6 weeks after the last rescue dose is administered.

In a further preferred embodiment of the present invention, subsequent maintenance dose(s) of mirikizumab are administered at 4 week intervals after administration of the first maintenance dose and subsequent further maintenance dose(s) of mirikizumab are administered at 4 week intervals after administration of the first further maintenance dose.

In an alternative preferred embodiment of the present invention, subsequent maintenance dose(s) of mirikizumab are administered at 12 week intervals after administration of the first maintenance dose and subsequent further maintenance dose(s) of mirikizumab are administered at 12 week intervals after administration of the first further maintenance dose.

FIGURES

FIG. 1 illustrates the population PK model-estimated average serum concentrations of mirikizumab in the clinical study.

FIG. 2 illustrates the rates at Week 12 for induction endpoints of interest relative to average concentration of mirikizumab in each dose group.

FIG. 3 plots a model-estimated average concentration of mirikizumab during induction in patients based on clinical response (upper panel) or clinical remission (lower panel) status.

FIG. 4 plots the observed Week 12 concentration of mirikizumab during induction in patients based on clinical response (upper panel) or clinical remission (lower panel) status.

FIG. 5 plots the model-simulated change in modified Mayo score (MMS) at Week 12 versus Week 12 concentration of mirikizumab.

DETAILED DESCRIPTION

UC is a form of colitis, an inflammatory disease of the intestine, usually the colon, which includes characteristic ulcers. Symptoms of active disease usually include diarrhea mixed with blood, usually accompanied with varying degrees of abdominal pain, from mild discomfort to severely painful cramps.

There are a number of methods for assessing the severity of disease, including the Mayo Score, the Modified Mayo Score (MMS) and Ulcerative Colitis Disease Activity Index (UCDAI).

The Mayo score is a composite instrument comprised of the following 4 subscores:

(i) Stool Frequency (SF): The SF subscore is a patient-reported measure. This item reports the number of stools in a 24-hour period, relative to the normal number of stools for that patient in the same period, on a 4-point scale. A stool is defined as a trip to the toilet when the patient has either a bowel movement, or passes blood alone, blood and mucus, or mucus only.

The total number of stools passed in a 24-hour period is recorded by the patient. The reference "normal" SF for that patient is typically recorded at the outset of a study or period of observation. Normal SF for that patient is on the reported SF when the patient was in remission or, if the patient has never achieved remission, the reported SF before initial onset of signs and symptoms of UC.

| Stool Frequency Sub score | Score |
| --- | --- |
| Normal number of stools for subject | 0 |
| 1 to 2 stools more than normal | 1 |
| 3 to 4 stools more than normal | 2 |
| 5 or more stools than normal | 3 |

(ii) Rectal Bleeding (RB): The RB subscore is a patient-reported measure. This item reports the most severe amount of blood passed per rectum for a given day, on a 4-point scale.

| Rectal Bleeding Subscore | Score |
| --- | --- |
| No blood seen | 0 |
| Streaks of blood with stool less than half of the time | 1 |
| Obvious blood (more than just streaks) or streaks of blood with stool most of the time | 2 |
| Blood alone passed | 3 |

(iii) Endoscopic Subscore (ES): The ES is a physician-reported measure that reports the worst appearance of the mucosa on flexible sigmoidoscopy or colonoscopy, on a 4-point scale. Consistent with current clinical practice, friability is excluded from the definition of an ES of 1.

| Endoscopic Subscore | Score |
| --- | --- |
| Normal or inactive disease | 0 |
| Mild disease (erythema, decreased vascular pattern) | 1 |
| Moderate disease (marked erythema, absent vascular pattern, friability, erosions) | 2 |
| Severe disease (spontaneous bleeding, ulceration) | 3 |

(iv) Physician's Global Assessment (PGA): The PGA is a physician-reported measure that summarizes the assessment of the patient's UC disease activity on a 4-point scale.

| Physician's Global Assessment | Score |
|---|---|
| Normal | 0 |
| Mild disease | 1 |
| Moderate disease | 2 |
| Severe disease | 3 |

Each subscore is scored on a 4-point scale, ranging from 0 to 3, to give a maximum Mayo score of 12.

The MMS is a modification made to the original Mayo Index reference (Schroeder et al., New Eng J Med, 317(26): 1625-1629, 1987) and includes 3 of the 4 subscores of the Mayo Score. It does not include the Physician's Global Assessment. The MMS evaluates three subscores, each on a scale of 0 to 3 with a maximum total score of 9. The following table summarizes the respective MMS subscales for scoring.

TABLE 1

Modified Mayo Score
Modified Mayo Score (MMS)

| Index | Stool Frequency (SF) | Rectal Bleeding (RB) | Endoscopy Score (ES) |
|---|---|---|---|
| MMS | 0 = Normal number of stools per day for this patient<br>1 = 1 to 2 more stools per day for this patient<br>2 = 3 to 4 more stools than normal<br>3 = 5 or more stools than normal | 0 = No blood seen<br>1 = streaks of blood with stool less than half the time<br>2 = obvious blood with stool most of the time<br>3 = blood alone passed | 0 = normal or inactive disease<br>1 = mild disease (erythema decreased vascular pattern)<br>2 = moderate disease (marked erythema, absent vascular pattern, friability erosions)<br>3 = severe disease (spontaneous bleeding, ulceration) |

Patients who have a Mayo Score of 6-12 or a MMS of 4-9, each with an ES of ≥2, are defined as having moderate to severely active ulcerative colitis.

As used herein, the term "biologic experienced" refers to patients that have been administered a biologic for example, an anti-TNF-α antibody, for the treatment of UC, in particular, for the treatment of moderate to severe UC. Such patients may or may not have been administered a conventional medicine for the treatment of UC. Conventional medicines for the treatment of UC include 5-aminosalicylic acid (5-ASA), steroids, and immunosuppressive drugs such as azathioprine (AZA) and 6-mercaptopurine (6-MP).

As used herein, the term "biologic-failed" refers to patients that have been administered a biologic, for example, an anti-TNF-α antibody, for the treatment of UC, in particular, for the treatment of moderate to severe UC. Such patients may or may not have been administered a conventional medicine for the treatment of UC. Conventional medicines for the treatment of UC 5-aminosalicylic acid (5-ASA), steroids, and immunosuppressive drugs such as azathioprine (AZA) and 6-mercaptopurine (6-MP). Such patients have an inadequate response to, loss of response to, or are intolerant to biologic therapy for UC (such as anti-TNF antibodies or anti-integrin antibodies) or to janus kinase (JAK) inhibitors (such as tofacitinib). In the context of the terms "biologic-failed", inadequate response means signs and symptoms of persistently active disease despite induction treatment at the approved induction dosing that was indicated in the product label at the time of use. In the context of the term "biologic-failed", loss of response is defined as recurrence of signs and symptoms of active disease during approved maintenance dosing following prior clinical benefit (discontinuation despite clinical benefit does not qualify as having failed or being intolerant to UC biologic therapy). In the context of the term "biologic-failed", intolerance means a history of intolerance to infliximab, adalimumab, golimumab, vedolizumab, tofacitinib or other approved biologics or JAK inhibitors (including but not limited to infusion-related event, demyelination, congestive heart failure, or any other drug-related AE that led to a reduction in dose or discontinuation of the medication).

As used herein, the term "biologic-naïve" refers to patients that have not been administered a biologic, for example, an anti-TNF-α antibody, for the treatment of UC, in particular, for the treatment of moderate to severe UC. Such patients may or may not have been administered a conventional medicine for the treatment of UC. Conventional medicines for the treatment of UC 5-aminosalicylic acid (5-ASA), steroids, and immunosuppressive drugs such as azathioprine (AZA) and 6-mercaptopurine (6-MP).

As used herein, the term "conventional-failed" refers to patients who have an inadequate response to, loss of response to, or are intolerant to at least one of the following medications:
(i) corticosteroids
Corticosteroid-refractory colitis is defined as signs and/or symptoms of active UC despite oral prednisone (or equivalent) at doses of at least 30 mg/day for a minimum of 2 weeks.
Corticosteroid-dependent colitis, defined as (a) an inability to reduce corticosteroids below the equivalent of prednisone 10 mg/day within 3 months of starting corticosteroids without a return of signs and/or symptoms of active UC and (b) a relapse within 3 months of completing a course of corticosteroids.
A history of intolerance of corticosteroids includes, but is not limited to, Cushing's syndrome, osteopenia/osteoporosis, hyperglycemia, or neuropsychiatric side-effects, including insomnia, associated with corticosteroid treatment).
(ii) immunomodulators:
signs and/or symptoms of persistently active disease despite at least 3 months' treatment with one of the following:
(a) oral AZA (≥1.5 mg/kg/day) or 6-MP (≥0.75 mg/kg/day), or
(b) oral AZA or 6-MP within a therapeutic range as judged by thioguanine metabolite testing, or
(c) a combination of a thiopurine and allopurinol within a therapeutic range as judged by thioguanine metabolite testing
A history of intolerance to at least one immunomodulator includes but is not limited to nausea/vomiting, abdominal pain, pancreatitis, liver function test abnormalities, and lymphopenia)
Conventional-failed patients have neither failed nor demonstrated an intolerance to a biologic medication (anti-TNF antibody or anti-integrin antibody) that is indicated for the treatment of UC.

Using the MMS, as used herein, "clinical remission" is defined as a RB subscore of 0, SF subscore of 0 or 1 (with ≥1-point decrease from baseline), and ES of 0 or 1 (excluding friability). Using the MMS, as used herein, "clinical response" is defined as achieving a decrease in 9-point MIMS subscore of ≥2 points and ≥30-35% from baseline, with either a decrease of RB subscore of ≥1 or a RB subscore of 0 or 1. Using the MMS, as used herein, "endoscopic remission" is defined as achieving a Mayo ES of 0. Using the MMS, as used herein, "endoscopic healing" is defined as having achieved a Mayo ES of 0 or 1. Using the MMS, as used herein "symptomatic remission" is defined as having achieved a SF=0 or SF=1 with a ≥1-point decrease from baseline, and a RB=0. Using the MMS, as used herein, "loss of response" is defined as is defined as: (a) ≥2-point increase from baseline in the combined stool frequency (SF) and rectal bleeding (RB) scores (b) combined SF and RB score of ≥4, on 2 consecutive visits ≥7 days apart with confirmation of negative *Clostridium difficile* testing and (c) endoscopic subscore (ES) of 2 or 3.

As used herein, "dose" or "dosing" refers to to the administration of a substance (for example, an anti-IL-23p19 antibody) to achieve a therapeutic objective (for example, the treatment of ulcerative colitis).

As used herein, "induction period" refers to a period of treatment of a patient comprising administration of an anti-IL-23p19 antibody to the patient in order to induce clinical remission, clinical response, endoscopic remission, endoscopic healing and/or symptomatic remission, each of these terms as defined above. There is no minimum or maximum duration of the "induction period but it is typically 4, 8 or 12 weeks in duration. The end of induction period is typically an end-of-induction assessment occurring 4 or 8 weeks after the last induction dose has been administered.

As used herein, "induction dose" refers to a first dose of an anti-IL-23p19 antibody administered to a patient in order to induce clinical remission, clinical response, endoscopic remission, endoscopic healing and/or symptomatic remission, each of these terms as defined above. The "induction dose" can be a single dose or, alternatively, a set of doses. The "induction dose" is administered during the induction period.

As used herein, "extended induction period" refers to a period of treatment of a patient comprising administration of an anti-IL-23p19 antibody to the patient that is required in order to induce clinical remission, clinical response, endoscopic remission, endoscopic healing and/or symptomatic remission, each of these terms as defined above, because clinical remission, clinical response, endoscopic remission, endoscopic healing and/or symptomatic remission was not achieved during an initial induction period. The "extended induction period" may be 4, 8 or 12 weeks in duration.

As used herein, "extended induction dose" refers to a further induction dose of an anti-IL-23p19 antibody administered to a patient in order to induce clinical remission, clinical response, endoscopic remission, endoscopic healing and/or symptomatic remission, each of these terms as defined above, because clinical remission, clinical response, endoscopic remission, endoscopic healing and/or symptomatic remission was not achieved during an initial induction period. The "extended induction dose" can be a single dose or, alternatively, a set of doses. There is no minimum or maximum duration of the "extended induction period but it is typically 4, 8 or 12 weeks in duration. The end of extended induction period is typically an end-of-extended induction assessment occurring 4 or 8 weeks after the last extended induction dose has been administered. The "extended induction dose" is administered during the extended induction period.

As used herein, "maintenance period" refers to refers to a period of treatment comprising administration of an anti-IL-23p19 antibody to a patient in order to maintain a desired therapeutic effect, the desired therapeutic effect being clinical remission, clinical response, endoscopic remission, endoscopic healing and/or symptomatic remission, each of these terms as defined above. The "maintenance period" follows the induction period or extended induction period, and, therefore, is initiated once a desired therapeutic effect—clinical remission, clinical response, endoscopic remission, endoscopic healing and/or symptomatic remission—is achieved.

As used herein, "maintenance dose" refers to a subsequent dose of an anti-IL-23p19 antibody administered to a patient to maintain or continue a desired therapeutic effect, namely, clinical remission, clinical response, endoscopic remission, endoscopic healing and/or symptomatic remission, each of these terms as defined above. A "maintenance dose" is administered subsequent to the induction dose. A "maintenance dose" can be a single dose or, alternatively, a set of doses.

In the context wherein a patient develops a loss of response during the maintenance period, re-achieves a desired therapeutic effect after administration of one or more rescue doses and is restarted on maintenance therapy, the maintenance dose is referred to as "further maintenance dose". The "maintenance dose" or "further maintenance dose" is administered during the maintenance period of therapy. The further maintenance dose and dosing intervals during the restarted maintenance period are typically the same as dose and dosing intervals during the initial maintenance period but may be changed if the attending health care professional has reason to believe that the patient may benefit from changes such as an increased dose of the anti-IL-23p19 antibody or more frequent dosing.

As used herein, the term "rescue dose" refers to a dose of an anti-IL-23p19 antibody administered to a patient that has developed a loss of response in order to re-induce/re-achieve the therapeutic effect achieved at the end of an induction period, the therapeutic effect being clinical remission, clinical response, endoscopic remission, endoscopic healing and/or symptomatic remission, each of these terms defined above.

As used herein, the term "rescue period" refers to a period of treatment of a patient comprising administration of an anti-IL-23p19 antibody to the patient in order to re-induce clinical remission the therapeutic effect achieved at the end of an induction period, the therapeutic effect being clinical response, endoscopic remission, endoscopic healing and/or symptomatic remission, each of these terms as defined above. The "rescue period" may be 4, 8 or 12 weeks in duration.

The rescue dose and dosing intervals during the rescue period are typically the same as dose and dosing intervals during the initial induction period but may be changed if the attending health care professional has reason to believe that the patient may benefit from changes such as an increased dose of the anti-IL-23p19 antibody or more frequent dosing.

As used herein, the terms "treating," "treat," or "treatment," refer to restraining, slowing, lessening, reducing, or reversing the progression or severity of an existing symptom, disorder, condition, or disease, or ameliorating clinical symptoms and/or signs of a condition. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. Those in need of treatment include those already with the disease.

As used herein, the term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a human IL-23. For example, antibody fragments capable of binding to IL-12/23 or portions thereof, including, but not limited to, Fab (e.g. by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g. by molecular biology techniques) fragments, are encompassed by the present invention (see, e.g. Colligan et al., Current Protocols in Immunology, John Wiley & Sons, NY, NY, (1994-2001)).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH1 domain and/or hinge region of the heavy chain. The various portions of antibodies can be joined together chemically by conventional techniques, or can be prepared as a contiguous protein using genetic engineering techniques.

As used herein "anti-IL-23p19 antibody" refers to an antibody that binds to the p19 subunit of human IL-23 but does not bind to the p40 subunit of human IL-23. An anti-IL-23p19 antibody thus binds to human IL-23 but does not bind to human IL-12.

Examples of anti-IL-23p19 antibodies that may be used in the methods of the present invention include guselkumab, tildrakizumab, risankizumab, mirikizumab and brazikumab.

Guselkumab, CAS Registry No. 1350289-85-8, is a fully human IgG$_1$ lambda monoclonal antibody that binds to the p19 subunit of human IL-23. The antibody and methods of making same are described in U.S. Pat. No. 7,935,344.

Tildrakizumab, CAS Registry No. 1326244-10-3, is a humanized, IgG1 kappa monoclonal antibody targeting the p19 subunit of human IL-23. The antibody and methods of making same are described in U.S. Pat. No. 8,293,883.

Risankizumab, CAS Registry No. 1612838-76-2, is a humanized, IgG1 kappa monoclonal antibody targeting the p19 subunit of human IL-23. The antibody and methods of making same are described in U.S. Pat. No. 8,778,346.

Mirikizumab, CAS Registry No. 1884201-71-1, is a humanized, IgG$_4$-kappa monoclonal antibody targeting the p19 subunit of human IL-23. The antibody and methods of making same are described in U.S. Pat. No. 9,023,358.

Brazikumab, CAS Registry No. 1610353-18-8, is a humanized, IgG$_2$-lambda monoclonal antibody targeting the p19 subunit of human IL-23. The antibody and methods of making same are described in U.S. Pat. No. 8,722,033.

The anti-IL-23p19 antibody, or pharmaceutical compositions comprising the same, may be administered by parenteral routes (e.g., subcutaneous, intravenous, intraperitoneal, intramuscular, or transdermal).

The term "intravenous infusion" refers to introduction of an agent into the vein of an animal or human patient over a period of time greater than approximately 15 minutes, generally between approximately 30 to 90 minutes.

The term "subcutaneous injection" refers to introduction of an agent under the skin of an animal or human patient, preferable within a pocket between the skin and underlying tissue, by relatively slow, sustained delivery from a drug receptacle. Pinching or drawing the skin up and away from underlying tissue may create the pocket.

Pharmaceutical compositions comprising an anti-IL-23p19 antibody for use in the methods of the present invention can be prepared by methods well known in the art (e.g., Remington: The Science and Practice a/Pharmacy, 19$^{th}$ edition (1995), (A. Gennaro et al., Mack Publishing Co.) and comprise an antibody as disclosed herein, and one or more pharmaceutically acceptable carriers, diluents, or excipients.

EXAMPLES

Example 1: Clinical Study

Overview

This study is a Phase 2, multicenter, randomized, double-blind, parallel, placebo-controlled study of mirikizumab in patients with moderate to severe ulcerative colitis (UC). Moderate to severe UC is defined as a MMS of 6 to 12, with an endoscopic subscore of ≥2. The study comprises of a screening period of up to a maximum of 28 days, a 12-week blinded intravenous therapy period, a 92-week subcutaneous therapy period for responders at Week 12, and a 92-week intravenous and subcutaneous extension for non-responders at Week 12.

Objectives

The primary objective was to test the hypothesis that treatment with mirikizumab is superior to placebo in inducing clinical remission after 12 weeks of treatment (Week 12).

Secondary objectives included the following:
  evaluation of the safety and tolerability of treatment with mirikizumab;
  evaluation of the efficacy of mirikizumab in inducing a clinical response at Week 12;
  evaluation of endoscopic remission at Week 12 and Week 52;
  evaluation of the effect of maintenance treatment with mirikizumab on the durability of clinical remission, endoscopic remission and clinical response at Week 52; and
  characterization of the pharmacokinetic (PK) profile of mirikizumab.

Endpoints were defined using the MMS, which is the 9-point Mayo score excluding the Physician's Global Assessment (PGA). Endoscopies are read centrally. Rates of endoscopic healing are also determined at Weeks 12 and 52. The endpoint definitions are as follows:
  Clinical remission: Having achieved the following Mayo subscores: a rectal bleeding (RB) subscore of 0, stool frequency (SF) subscore of 0 or 1 (with 1-point decrease from baseline), and endoscopy subscore of 0 or 1.
  Clinical response: Having achieved a decrease in 9-point Mayo subscore of ≥2 points and ≥35% from baseline, with either a decrease of RB subscore of ≥1 or a RB subscore of 0 or 1.
  Endoscopic remission: Having achieved a Mayo ES of 0.
  Endoscopic healing: Having achieved a Mayo ES of 0 or 1.

Methods

This study comprises a screening period, two treatment periods for responders at Week 12 (a 12-week blinded intravenous induction period and a 92-week subcutaneous maintenance period) and two treatment periods for non-responders at Week 12 who wish to continue in the study (a 12-week blinded intravenous induction period and a 92-week intravenous and subcutaneous extension period). Approximately two-thirds of the patients randomized to study treatment have previously been exposed to at least one biologic therapy (TNF antagonist or vedolizumab), and approximately one-third of the patients are naive to biologic therapy.

a) Screening Period

Patients are evaluated for study eligibility ≤28 days before the baseline visit. At the baseline visit, patients who fulfill the eligibility criteria are randomized equally to 1 of 4 induction treatment arms.

Eligible patients are male or female patients aged 18-75 years at the time of initial screening, with moderately to severely active UC as defined by a Mayo score of 6 to 12 (or a MMS of 4-9) with an endoscopic subscore≥2 within 14 days before the first dose of study treatment, and have evidence of UC extending proximal to the rectum (≥15 cm of involved colon). Patients must either:

(a) be naive to biologic therapy (e.g. TNF antagonists or vedolizumab) and have at least 1 of the following:
    inadequate response or failure to tolerate current treatment with oral or IV corticosteroids or immunomodulators (6-MP or AZA) or
    history of corticosteroid dependence (an inability to successfully taper corticosteroids without return of UC)
    or
(b) have also received treatment with 1 or more biologic agents (such as TNF antagonists or, vedolizumab, or experimental UC therapeutics; biologics or oral kinase inhibitors) at doses approved for the treatment of UC with or without documented history of failure to respond to or tolerate such treatment.

Patients may be receiving a therapeutic dosage of the following drugs:

(a) oral 5-ASA compounds: if the prescribed dose has been stable for at least two weeks before baseline;
(b) oral corticosteroid therapy (prednisone≤20 mg/d or equivalent): if the prescribed dose has been stable for at least the 2 weeks before baseline;
(c) AZA or 6-MP: if the prescribed dose has been stable for at least 8 weeks before baseline.

b) Induction Period

A 12-week induction period is designed to establish the efficacy and safety of mirikizumab administered IV at Weeks 0, 4, and 8 compared to placebo. At Week 0 (baseline), patients are enrolled into four induction treatment arms (placebo, 50 mg mirikizumab, 200 mg mirikizumab or 600 mg mirikizumab) to adequately evaluate the clinical response and remission endpoints. Patients enrolled in the trial are stratified across the treatment arms on the basis of previous exposure to biologic therapy for treatment of UC. Blinded study drug (mirikizumab or placebo) is administered at Weeks 0, 4 and 8.

Exposure-based dose adjustment was used for two mirikizumab dose groups based on plasma concentrations of mirikizumab. Dose levels in patients in the 50-mg mirikizumab and 200-mg mirikizumab groups could be increased at the Week 4 and Week 8 visits if the projected trough concentrations for those visits fell below pre-specified thresholds. Patients in the 600-mg mirikizumab dose group remained on a fixed dose throughout the induction period.

c) Maintenance Period

The maintenance period is designed to explore the safety and durability of clinical responses and remissions to treatment with 200 mg mirikizumab administered SC Q4W or Q12W. Patients who achieved response with blinded mirikizumab induction dosing are re-randomized to one of two mirikizumab maintenance treatment arms (200 mg every 4 weeks [Q4W] subcutaneous (SC) or 200 mg every 12 weeks [Q12W] SC). Patients in the placebo arm achieving a clinical response remain on placebo. Patients having clinical responses at Week 12 continue study participation in the maintenance period up to Week 52. Patients entering the mirikizumab maintenance dosing period are stratified according to their Week-12 remission status.

d) Extension Period

Patients who are randomized in the induction period but do not have a clinical response at Week 12 have the option to continue in a study extension period or discontinue from the study. The extension period consists of induction and maintenance parts that are modified versions of the induction and maintenance periods in the primary study design. During the extension period induction, patients receive 600 mg or 1000 mg mirikizumab IV administered at extension Weeks 0, 4, and 8. Patients who have a clinical response with extension period induction dosing have the opportunity to continue on extension period maintenance therapy, while non-responders during the extension period are discontinued from the study. Patients who continue into the extension period maintenance treatment receive 200 mg of mirikizumab administered SC Q4W (unblinded).

Study Summary

There were a total of 249 patients in the intent-to-treat (ITT) population. Demographic characteristics were balanced between the mirikizumab group (total) and placebo (total). Of the 249 randomized patients, 100 patients were female. The mean age (±standard deviation) was 42.6 years (±13.9 years).

Disease characteristics were balanced between the total mirikizumab treatment group and placebo. Approximately 42% of patients had moderately active disease at baseline (Mayo score 6 to 8: placebo 42.9%; total mirikizumab 41.8%), whereas approximately 58% had severely active disease at baseline (Mayo score 9 to 12: placebo 57.1%; total mirikizumab 58.2%). In the MMS, fecal calprotectin and C-reactive protein (CRP) at baseline were all balanced between groups.

There were no significant differences between the total mirikizumab group and placebo with respect to the proportion of patients receiving oral corticosteroids or 5-aminosalicylates at baseline. A greater proportion of patients in the placebo group received thiopurine therapy at baseline compared with the total mirikizumab group (total mirikizumab 23.1%; placebo 39.7%).

Results: Summary

Endoscopic videos were read centrally by experts blinded to treatment allocation and time point. Comparisons of rates of clinical remission (primary outcome), clinical response, endoscopic healing endoscopic remission, and symptomatic remission were made using logistic regression analysis. Baseline characteristics were similar among treatment groups. Most patients (63%) had been either exposed to or failed therapy with a biologic.

At Week 12, clinical remission rates were greater (p<0.01) in patients treated with mirikizumab 200-mg, but not mirikizumab 50-mg or mirikizumab 600-mg, compared to placebo-treated patients (Table). Clinical response rates at Week 12 were greater (p<0.05) for all mirikizumab groups, compared to placebo group. Endoscopic healing rates were greater (p<0.05) for the mirikizumab 50 and 200-mg groups compared to placebo-treated patients. Endoscopic remission rates were similar between all groups. Symptomatic remission rates were greater (p<0.01) for mirikizumab 200 and 600 mg groups compared to placebo-treated patients. Although mirikizumab exposure increased with dose, efficacy did not follow a typical plateauing dose or exposure response. There were similar rates of serious adverse events (SAEs) and treatment-emergent adverse events (TEAEs) across the treatment groups.

Taken together, the Week 12 outcome data indicate that patients in the 200-mg mirikizumab group responded better to treatment at Week 12 than patients in the placebo or 50-mg mirikizumab group. Furthermore, patients in the 200-mg mirikizumab group responded better to treatment at Week 12 than patients in the 600-mg mirikizumab group.

Based on the efficacy data available for the maintenance period of this study, the two mirikizumab SC dosing regimens of 200 mg Q4W and 200 mg Q12W were observed to have similar clinical remission, clinical response, and endoscopic healing rates at Week 52. Baseline (BL) characteristics of patients who entered the maintenance period were similar between groups. At BL, 52.7% had previously received a biologic. At Week 52, 46.8% (Q4W) and 37.0% (Q12W) were in clinical remission. Additionally, 80.9% (Q4W) and 76.1% (Q12W) had clinical response, and 57.4% (Q4W) and 47.8% (Q12W) had an ES=0/1. Among those in clinical remission at Week 12, 61.1% (Q4W) and 38.5% (Q12W) remained in clinical remission at Week 52. Among those in clinical response (but not remission) at Week 12, 37.9% (Q4W) and 36.4% (Q12W) achieved clinical remission at Week 52. During the maintenance period, 1 patient discontinued study due to an adverse event (AE), and similar frequencies of treatment-emergent AEs and serious AEs were reported across both treatment groups. Mirikizumab thus demonstrated durable efficacy (assessed by multiple measures) with no unexpected safety signals and few discontinuations due to AEs throughout the maintenance period.

Analyses of mirikizumab concentration data indicated that exposure increased in proportion to dose. Exposure was a significant predictor of change from baseline in the Week 12 MMS but there was not a strong relationship between individual patient exposure and clinical response or remission.

During maintenance, the Q12W regimen produced a more intermittent mirikizumab concentration profile, whereas the Q4W concentration profile was more consistent. The Q4W regimen also produced trough concentrations that were similar to the Week 12 trough concentration produced in the 200-mg induction cohort.

Mirikizumab was generally well tolerated, with few discontinuations due to adverse events (AEs). There were no clinically significant safety findings, and no dose relationship was noted in the induction or maintenance periods. Across all groups, treatment-emergent adverse events (TEAEs) were generally mild or moderate in severity. There were no deaths.

Results: Week 12—Efficacy

Endoscopic videos were read centrally by experts blinded to treatment allocation and time point. Comparisons of rates of clinical remission (primary outcome), clinical response, endoscopic healing, endoscopic remission, and symptomatic remission were made using logistic regression analysis.

The primary, secondary and key exploratory endpoint data at Week 12 (non-responder, imputation [NRI], ITT population) are summarized in Table 2.

TABLE 2

Summary of Efficacy Measures at Week 12

|  | Placebo IV Q4W (N = 63) | Miri IV Q4W 50 mg$^a$ (N = 63) | Miri IV Q4W 200 mg$^a$ (N = 62) | Miri IV Q4W 600 mg (N = 61) |
|---|---|---|---|---|
| Clinical remission | | | | |
| Nx | 59 | 61 | 60 | 57 |
| n (%) | 3 (4.8%) | 10 (15.9%) | 14 (22.6%) | 7 (11.5%) |
| 95% CI$^b$ | (0.0%, 10.0%) | (6.8%, 24.9%) | (12.2%, 33.0%) | (3.5%, 19.5%) |
| Difference vs placebo |  | 11.1% | 17.8% | 6.7% |
| 95% CI$^b$ |  | (0.7%, 21.6%) | (6.2%, 29.5%) | (−2.9%, 16.3%) |
| p-value vs placebo$^c$ |  | 0.066 | 0.004 | 0.142 |
| Clinical response | | | | |
| Nx | 59 | 61 | 60 | 57 |
| n (%) | 13 (20.6%) | 26 (41.3%) | 37 (59.7%) | 30 (49.2%) |
| 95% CI$^b$ | (10.6%, 30.6%) | (29.1%, 53.4%) | (47.5%, 71.9%) | (36.6%, 61.7%) |
| Difference vs placebo |  | 20.6% | 39.0% | 28.5% |
| 95% CI$^b$ |  | (4.9%, 36.4%) | (23.3%, 54.8%) | (12.5%, 44.6%) |
| p-value vs placebo$^c$ |  | 0.014 | <0.001 | 0.001 |
| Endoscopic healing | | | | |
| Nx | 59 | 61 | 60 | 57 |
| n (%) | 4 (6.3%) | 15 (23.8%) | 19 (30.6%) | 8 (13.1%) |
| 95% CI$^b$ | (0.3%, 12.4%) | (13.3%, 34.3%) | (19.2%, 42.1%) | (4.6%, 21.6%) |
| Difference vs placebo |  | 17.5% | 24.3% | 6.8% |
| 95% CI$^b$ |  | (5.3%, 29.6%) | (11.3%, 37.3%) | (−3.6%, 17.2%) |
| p-value vs placebo$^c$ |  | 0.012 | <0.001 | 0.215 |
| Histologic remission | | | | |
| Nx |  | 53 | 54 | 55 | 52 |
| n (%) | 10 (18.9%) | 7 (13.0%) | 25 (45.5%) | 19 (36.5%) |

TABLE 2-continued

Summary of Efficacy Measures at Week 12

|  | Placebo IV Q4W (N = 63) | Miri IV Q4W 50 mg$^a$ (N = 63) | Miri IV Q4W 200 mg$^a$ (N = 62) | Miri IV Q4W 600 mg (N = 61) |
|---|---|---|---|---|
| 95% CI$^b$ | (8.3%, 29.4%) | (4.0%, 21.9%) | (32.3%, 58.6%) | (23.5%, 49.6%) |
| Difference vs placebo |  | −5.9% | 26.6% | 17.7% |
| 95% CI$^b$ |  | (−19.7%, 7.9%) | (9.7%, 43.4%) | (0.9%, 34.5%) |
| p-value vs placebo$^c$ |  | 0.411 | 0.004 | 0.044 |
| Endoscopic remission | | | | |
| Nx | 59 | 61 | 60 | 57 |
| n (%) | 1 (1.6%) | 2 (3.2%) | 2 (3.2%) | 1 (1.6%) |
| 95% CI$^b$ | (0.0%, 4.7%) | (0.0%, 7.5%) | (0.0%, 7.6%) | (0.0%, 4.8%) |
| Difference vs placebo |  | 1.6% | 1.6% | 0.1% |
| 95% CI$^b$ |  | (−3.7%, 6.9%) | (−3.7%, 7.0%) | (−4.4%, 4.5%) |
| p-value vs placebo$^c$ |  | NA | NA | NA |

Abbreviations: CI = confidence interval; ES = endoscopic subscore; ITT = intent-to-treat population; IV = intravenous; Miri = mirikizumab; N = number of patients in the analysis population; n = number of patients in the specified category; NA = not applicable; NRI = non-responder imputation; Nx = number of patients in the analysis with non-missing data; Q4W = every 4 weeks; RB = rectal bleeding; SF = stool frequency; vs = versus.
$^a$A total of 73% of patients in the 50-mg group and 44% of patients in the 200-mg group had exposure-based dose adjustments before Week 12, resulting in mean mirikizumab doses of 100 mg and 250 mg, respectively.
$^b$Confidence intervals are calculated using Wald method.
$^c$Logistic regression analysis with geographic region and prior biologic experience as factors.
Note:
Percentage of response is calculated by n/Nx*100%. Clinical remission at Week 12 is defined as achieving a RB Mayo subscore of 0, SF Mayo subscore of 0 or 1 (with 1-point decrease from baseline) and Mayo ES of 0 or 1. Clinical response at Week 12 is defined as achieving at Week 12 a decrease in the 9-point Mayo subscores (comprising the subscores of RB, SF, and the endoscopic findings) inclusive of ≥2 points and ≥35% from baseline with either a decrease of RB subscore of ≥1 or a RB subscore of 0 or 1. Endoscopic healing is defined as achieving an endoscopic findings subscore of 0 or 1. Histologic remission is defined as Geboes histologic subscores of 0 for the neutrophils in lamina propria, neutrophils in epithelium, and erosion or ulceration parameters. Endoscopic remission at Week 12 is defined as achieving a Mayo endoscopic score of 0 at Week 12.

At Week 12, clinical remission rates were greater (p<0.01) in patients treated with 200-mg mirikizumab, but not 50-mg mirikizumab or 600-mg mirikizumab, compared to placebo-treated patients. Clinical response rates at Week 12 were greater (p<0.05) for all mirikizumab groups compared to the placebo group. Endoscopic healing rates were greater (p<0.05) for the 50-mg mirikizumab and 200-mg mirikizumab groups compared to placebo-treated patients. Endoscopic remission rates were similar between all groups. Symptomatic remission rates were greater (p<0.01) for 200-mg and 600-mg mirikizumab groups compared to placebo-treated patients.

Overall, significant efficacy relative to placebo was observed at Week 12 in the 50-mg and 200-mg IV Q4W groups in the study and the maximum efficacy was observed in the 200-mg IV Q4W groups. Due to the application of exposure-based dose adjustments, the overall average induction dose received by patients in the 50-mg and 200-mg cohorts were 100 mg and 250 mg, respectively. Although mirikizumab exposure increased in proportion to dose, patients in the 600-mg mirikizumab group did not respond better to treatment at Week 12 than patients in the 200-mg mirikizumab group.

Results: Week 12—Efficacy by Prior Biologic Therapy

To determine if patients that were naïve to biologic therapy had better clinical outcomes than patients who had been previously exposed to biologics, clinical remission, clinical response and endoscopic healing data were examined by prior biologic subgroup (biologic experienced vs. biologic naïve).

Clinical remission, clinical response and endoscopic healing rates at Week 12 were higher in biologic-naïve patients compared with biologic-experienced patients (see Tables 3-5).

Clinical remission rates in the biologic-naïve 200-mg mirikizumab group were higher than placebo (36.4% versus 8.7%, p=0.035, Table 3).

Clinical response rates in the biologic-naïve 200-mg mirikizumab (72.7% versus 34.8%, p=0.017) and the biologic-experienced 200-mg mirikizumab (52.5% versus 12.5%, p<0.001) and 600-mg mirikizumab (42.1% versus 12.5%, p=0.005) were higher than placebo (Table 4).

Endoscopic healing rates were higher than placebo in the biologic-naïve 50-mg mirikizumab (37.5% versus 8.7%, p=0.036) and 200-mg mirikizumab groups (50.0% versus 8.7%, p=0.003, Table 5).

TABLE 3

Subgroup Analysis - Clinical Remission Rates Based on MMS at Week 12 by Prior Biologic-Experienced versus Prior Biologic-Naive

| Subgroup | Placebo IV Q4W (N = 63) | Miri IV Q4W 50 mg$^a$ (N = 63) | Miri IV Q4W 200 mg$^a$ (N = 62) | Miri IV Q4W 600 mg (N = 61) |
|---|---|---|---|---|
| Prior Biologic Therapy | | | | |
| Ns | 40 | 39 | 40 | 38 |
| n (%) | 1 (2.5%) | 3 (7.7%) | 6 (15.0%) | 3 (7.9%) |
| Biologic-Naive | | | | |
| Ns | 23 | 24 | 22 | 23 |
| n (%) | 2 (8.7%) | 7 (29.2%) | 8 (36.4%)* | 4 (17.4%) |

Abbreviations: IV = intravenous; Miri = mirikizumab; N = number of patients in the analysis population; n = number of patients in the specified category; NRI = non-responder imputation; Ns = number of patients in each subgroup; Q4W = every 4 weeks.
$^a$A total of 73% of patients in the 50-mg group and 44% of patients in the 200-mg group had exposure-based dose adjustments before Week 12, resulting in mean mirikizumab doses of 100 mg and 250 mg, respectively.
Note:
p-value versus placebo:
*p < 0.05. p-value is from the Fisher's exact test. Percentage of response is calculated by n/Ns*100%.

TABLE 4

Subgroup Analysis - Clinical Response Rates based on MMS at Week 12 by Prior Biologic-Experienced versus Prior Biologic-Naive

| Subgroup | Placebo IV Q4W (N = 63) | Miri IV Q4W 50 mg$^a$ (N = 63) | Miri IV Q4W 200 mg$^a$ (N = 62) | Miri IV Q4W 600 mg (N = 61) |
|---|---|---|---|---|
| Prior Biologic Therapy | | | | |
| Ns | 40 | 39 | 40 | 38 |
| n (%) | 5 (12.5%) | 11 (28.2%) | 21 (52.5%)*** | 16 (42.1%)** |
| Biologic-Naive | | | | |
| Ns | 23 | 24 | 22 | 23 |
| n (%) | 8 (34.8%) | 15 (62.5%) | 16 (72.7%)* | 14 (60.9%) |

Abbreviations: IV = intravenous; Miri = mirikizumab; N = number of patients in the analysis population; n = number of patients in the specified category; NRI = non-responder imputation; Ns = number of patients in each subgroup; Q4W = every 4 weeks.
$^a$A total of 73% of patients in the 50-mg group and 44% of patients in the 200-mg group had exposure-based dose adjustments before Week 12, resulting in mean Miri doses of 100 mg and 250 mg, respectively.
Note:
p-value versus placebo:
*p < 0.05;
**p < 0.01;
***p < 0.001. p-value is from the Fisher's exact test.
Percentage of response is calculated by n/Ns*100%.

TABLE 5

Subgroup Analysis - Endoscopic Healing Rates at Week 12 by Prior Biologic-Experienced versus Prior Biologic-Naive

| Subgroup | Placebo IV Q4W (N = 63) | Miri IV Q4W 50 mg[a] (N = 63) | Miri IV Q4W 200 mg[a] (N = 62) | Miri IV Q4W 600 mg (N = 61) |
|---|---|---|---|---|
| Prior Biologic Therapy | | | | |
| Ns | 40 | 39 | 40 | 38 |
| n (%) | 2 (5.0%) | 6 (15.4%) | 8 (20.0%) | 4 (10.5%) |
| Biologic-Naive | | | | |
| Ns | 23 | 24 | 22 | 23 |
| n (%) | 2 (8.7%) | 9 (37.5%)* | 11 (50.0%)** | 4 (17.4%) |

Abbreviations: IV = intravenous: Miri = mirikizumab; N = number of patients in the analysis population; n = number of patients in the specified category; NRI = nonresponder imputation: Ns = number of patients in each subgroup; Q4W = every 4 weeks.
[a]A total of 73% of patients in the 50-mg group and 44% of patients in the 200-mg group had exposure-based dose adjustments before Week 12, resulting in mean Miri doses of 100 mg and 250 mg, respectively.
Note:
p-value versus placebo:
*p < 0.05;
**p < 0.01. p-value is from the Fisher's exact test. Percentage of response is calculated by n/Ns*100%.

Rates of clinical remission, clinical response and endoscopic healing were higher in biologic-naïve patients who received mirikizumab compared with biologic-experienced patients.

Results: Maintenance Period—Week 52

Patients in clinical response at Week 12 were re-randomized to receive either 200-mg mg mirikizumab SC Q4W or 200-mg mirikizumab SC Q12W. There was no randomized withdrawal to placebo group in maintenance. The interim primary, secondary, and key exploratory endpoint data at Week 52 are summarized in Tables 6a and 6b. The final primary, secondary, and key exploratory endpoint data at Week 52 are summarized in Table 7.

Rates for each efficacy measure at the interim Week 52 read-out shown in Tables 6a and 6b were comparable between the mirikizumab Q4W and Q12W maintenance groups, except for endoscopic remission, which was numerically higher in the Q12W group.

TABLE 6a

Summary of Efficacy Measures at Week 52

| | 200 mg Miri SC Q4W | | | 200 mg Miri SC Q12W | | |
|---|---|---|---|---|---|---|
| | n/N | % | (95% CI) | n/N | % | (95% CI) |
| Clinical remission | 10/23 | 43.48% | (23.2%, 63.7%) | 9/23 | 39.13% | (19.2%, 59.1%) |
| Clinical response | 18/23 | 78.26% | (61.4%, 95.1%) | 16/23 | 69.57% | (50.8%, 88.4%) |
| Endoscopic healing | 12/23 | 52.17% | (31.8%, 72.6%) | 13/23 | 56.52% | (36.3%, 76.8%) |
| Endoscopic remission | 3/23 | 13.04% | (0.0%, 26.8%) | 10/23 | 43.48% | (23.2%, 63.7%) |
| Symptomatic remission | 18/24 | 75.00% | (57.7%, 92.3%) | 14/23 | 60.87% | (40.9%, 80.8%) |
| Symptomatic response | 18/24 | 75.00% | (57.7%, 92.3%) | 16/23 | 69.57% | (50.8%, 88.4%) |

Abbreviations:
CI = confidence interval;
Miri = mirikizumab;
N = number of patients who either discontinued during the maintenance period or had data available for the Week 52 visit;
n = number of patients in the specified category;
Q4W = every 4 weeks;
Q12W = every 12 weeks;
SC = subcutaneous.
Note:
Confidence intervals were calculated using Wald method.

TABLE 6b

Durable Clinical Remission at Week 52

| 200 mg Miri SC Q4W | | | 200 mg Miri SC Q12W | | |
|---|---|---|---|---|---|
| n/Nx | % | (95% CI) | n/Nx | % | (95% CI) |
| 6/8 | 75.0% | (45.0%, 100%) | 3/5 | 60.00% | (17.1%, 100%) |

Abbreviations: CI = confidence interval; Miri = mirikizumab; Nx = number of Week 12 remitters who had had data available for the Week 52 visit: n = number of patients in the specified category; Q4W = every 4 weeks; Q12W = every 12 weeks; SC = subcutaneous.
Note:
Percentage of response was calculated by n/Nx*100%. Confidence intervals were calculated using Wald method. Durable clinical remission at Week 52 is defined as clinical remission at Week 52 for patients who had clinical remission at Week 12.

TABLE 7

Primary, secondary, and key exploratory endpoint data at Week 52

| | Treatment Groups (Wk-12 clinical responders) | | |
|---|---|---|---|
| Mean (SD) unless otherwise specified | Miri 200 mg Q4W (N = 47) | Miri 200 mg Q12W (N = 46) | Total miri (N = 93) |
| Baseline characteristics | | | |
| Age, years | 41.3 (14.1) | 38.9 (12.4) | 40.1 (13.3 |
| Male, n (%) | 27 (57.4) | 22 (47.8) | 49 (52.7) |
| Weight, kg | 74.6 (17.3) | 72.5 (18.0) | 73.5 (17.5) |
| Concomitant UC therapy, n (%) | | | |
| Corticosteroid | 22 (46.8) | 19 (41.3) | 41 (44.1) |
| 5-ASA | 37 (78.7) | 40 (87.0) | 77 (82.8) |
| Thiopurines | 15 (31.9) | 9 (19.6) | 24 (25.8) |
| Number of previous biologic therapies, n (%) | | | |
| 0 | 21 (44.7) | 23 (50.0) | 44 (47.3) |
| 1 | 12 (25.5) | 17 (37.0) | 29 (31.2) |
| 2 | 10 (21.3) | 5 (10.9) | 15 (16.1) |
| ≥3 | 4 (8.5) | 1 (2.2) | 5 (5.4) |

TABLE 7-continued

Primary, secondary, and key exploratory endpoint data at Week 52

| Mean (SD) unless otherwise specified | Treatment Groups (Wk-12 clinical responders) | | |
|---|---|---|---|
| | Miri 200 mg Q4W (N = 47) | Miri 200 mg Q12W (N = 46) | Total miri (N = 93) |
| Modified Mayo score | 6.0 (1.4) | 6.1 (1.4) | — |
| Week 52 (NRI) | | | |
| Clinical remission[a], n (%) | 22 (46.8) | 17 (37.0) | 39 (41.9) |
| Clinical response[b], n (%) | 38 (80.9) | 35 (76.1) | 73 (78.5) |
| ES = 0/1[c], n (%) | 27 (57.4) | 22 (47.8) | 49 (52.7) |
| ES = 0[d], n (%) | 7 (14.9) | 13 (28.3) | 20 (21.5) |
| Symptomatic remission[e], n (%) | 36 (76.6) | 30 (65.2) | 66 (71.0) |
| TEAE, n (%) | 36 (76.6) | 31 (67.4) | 67 (72.0) |
| SAE, n (%) | 2 (4.3) | 1 (2.2) | 3 (3.2) |
| Discontinuations due to AE, n (%) | 0 (0.0) | 1 (2.2) | 1 (1.1) |

[a]Clinical remission: 9-point Mayo score: rectal bleeding (RB) subscore = 0, stool frequency subscore = 0 or 1 with ≥1 point decrease from baseline, and endoscopy subscore = 0 or 1
[b]Clinical response: Decrease in 9-point Mayo score ≥2 points and ≥35% from baseline, and either a decrease in RB subscore ≥1 or RB subscore of 0 or 1
[c]ES = 0/1: centrally read Mayo endoscopic subscore = 0 or 1
[d]ES = 0: centrally read Mayo endoscopic subscore = 0
[e]Symptomatic remission: Stool frequency subscore = 0 or 1 and rectal bleeding subscore = 0
[1]Sandborn W J, et al. Presented at DDW 2018: 882-Efficacy and Safety of Anti-Interleukin-23 Therapy with Mirikizumab (LY3074828) in Patients with Moderate-To-Severe Ulcerative Colitis in a Phase 2 Study. Gastroenterology. 2018 May 31; 154(6): S-1360.
AE = Adverse Event; Nx = number of evaluable patients; NRI = non-responder imputation; SAE = Serious Adverse Event; TEAE = treatment-emergent adverse events At the final Week 52 read-out, among those in clinical remission at Week 12, 61.1% (Q4W) and 38.5% (Q12W) remained in clinical remission at Week 52. Among those in clinical response (but not remission) at Week 12, 37.9% (Q4W) and 36.4% (Q12W) achieved clinical remission at Week 52. Mirikizumab thus demonstrates durable efficacy Results: Extension Period—Week 12

Patients randomized to either placebo or mirikizumab induction treatment and who were not in clinical response at Week 12 were eligible to enter the extension period, which comprises two parts: a 12-week extension induction period followed by a 28-week extension maintenance period. In the extension induction period, patients received continued induction treatment with a fixed dose of 600-mg of mirikizumab IV Q4W at Weeks 0, 4 and 8, with an assessment of efficacy at Extension Week 12. To explore whether a higher extension induction dose may be associated with improved outcomes, the dose was increased to 1000-mg of mirikizumab IV Q4W.

Of the patients who received extension induction treatment with mirikizumab, 50.0% treated with 600-mg of mirikizumab IV Q4W and 43.8% treated with 1000-mg of mirikizumab IV Q12W, respectively, achieved clinical response, 15.0% and 9.4% achieved clinical remission, 20.0% and 15.6% achieved an endoscopic score of 0/1, and 0 and 3.0% had an endoscopic score of 0 at the end of the extended induction period (Week 24). Among placebo non-responders, 58.0% and 71.9% receiving 12 weeks of 600 mg or 1000 mg of mirikizumab IV Q4W, respectively, achieved clinical response, 25.0% and 25.0% achieved clinical remission, 25.0% and 37.5% achieved an endoscopic score of 0/1, and 0 and 9.4% achieved and endoscopic score of 0 at the end of the extended induction (Week 24). Treatment-emergent adverse events (AEs), discontinuations due to AE, and serious AEs were similar across treatment groups during the extended induction period.

TABLE 8

Extended Induction Treatment Groups (Week 12 clinical non-responders)

| Week 24 | Extended Induction mirikizumab non-responders | | Extended Induction placebo non-responders | |
|---|---|---|---|---|
| | OL EI Miri 600 mg Q4W (N = 20) | OL EI Miri 1000 mg Q12W (N = 64) | OL EI Miri 600 mg Q4W (N = 12) | OL EI Miri 1000 mg Q4W (N = 32) |
| Clinical response[a], n (%) | 10 (50.0) | 28 (43.8) | 7 (58.3) | 23 (71.9) |
| Clinical remission[b], n (%) | 3 (15.0) | 6 (9.4) | 3 (25.0) | 8 (25.0) |
| ES = 0/1[c], n (%) | 4 (20.0) | 10 (15.6) | 3 (25.0) | 12 (37.5) |
| ES = 0[d], n (%) | 0 (0) | 2 (3.1) | 0 (0) | 3 (9.4) |
| Treatment-emergent AEs, n (%) | 12 (60.0) | 31 (48.4) | 5 (41.7) | 14 (43.8) |
| Serious AEs, n (%) | 0 (0.0) | 2 (3.1) | 1 (8.3) | 3 (9.4) |
| Discontinuations from study due to AE, n (%) | 0 (0.0) | 3 (4.7) | 0 (0.0) | 1 (3.1) |

[a]Clinical response: Decrease in 9-point MMS ≥2 points and ≥35% from baseline, and either a decrease in rectal bleeding (RB) subscore ≥1 or RB subscore of 0 or 1
[b]Clinical remission: 9-point Mayo score: RB subscore = 0, stool frequency subscore = 0 or 1 with ≥1 point decrease from baseline, and endoscopy subscore = 0 or 1
[c]ES = 0/1: centrally read Mayo endoscopic subscore = 0 or 1
[d]ES = 0: centrally read Mayo endoscopic subscore = 0
AE = Adverse Event; EI = Extended Induction; OL = Open Label; NR = no clinical response at induction Week 12 (non-responder)

Extended induction and maintenance dosing with mirikizumab demonstrated efficacy (assessed by multiple measures) up to study Week 52. Importantly, an additional 12 weeks of extended induction with mirikizumab allowed 43.8-50.0% of induction mirikizumab non-responders to achieve clinical response. 65.8% of these patients had clinical response at Week 52 with mirikizumab 200 mg SC Q4W.

Results: Safety

Mirikizumab was well tolerated with few discontinuations due to adverse events (AEs). The incidences of serious adverse events (SAEs) and treatment emergent adverse events (TEAEs) were similar between placebo and mirikizumab treatment groups, with no dose relationship noted in the induction or maintenance periods. There were no deaths during the study. Overviews of AEs by induction, maintenance and extension study periods are shown in Tables 9-11.

TABLE 9

Overview of Adverse Events - Induction Period

| Number of Patients[b] | PBO IV Q4W (N = 63) n (%) | Miri IV Q4W 50 mg* (N = 63) n (%) | Miri IV Q4W 200 mg* (N = 62) n (%) | Miri IV Q4W 600 mg (N = 60) n (%) | Miri Total (n = 185) n (%) | Total (n = 248) n (%) | p-value[a] Miri Total vs PBO |
|---|---|---|---|---|---|---|---|
| Deaths[c] | 0 (0.0) | 0 (0.0) | 0 (0.0) | 0 (0.0) | 0 (0.0) | 0 (0.0) | >0.999 |
| SAEs | 2 (3.2) | 0 (0.0) | 2 (3.2) | 3 (5.0) | 5 (2.7) | 7 (2.8) | >0.999 |
| Discontinuations from study due to an AE | 3 (4.8) | 0 (0.0) | 1 (1.6) | 2 (3.3) | 3 (1.6) | 6 (2.4) | 0.173 |
| TEAEs | 32 (50.8) | 36 (57.1) | 32 (51.6) | 32 (53.3) | 100 (54.1) | 132 (53.2) | 0.664 |
| TEAEs related to study treatment by investigator[d] | 10 (15.9) | 12 (19.0) | 7 (11.3) | 11 (18.3) | 30 (16.2) | 40 (16.1) | >0.999 |

Abbreviations:

AE = adverse event;

IV = intravenous;

Miri = mirikizumab;

n = number of patients with at least 1 adverse event per event type;

N = number of patients in the safety population;

PBO = placebo;

Q4W = every 4 weeks;

SAE = serious adverse event;

TEAE = treatment-emergent adverse event;

vs = versus.

[a]Between-group comparisons were made using Fisher's Exact test. No adjustments for multiplicity were made.

[b]Patients may be counted in more than 1 category.

[c]Deaths were also included as SAEs and discontinuations due to AEs.

[d]Includes events that were considered related to study treatment as judged by the investigator.

*A total of 73% of patients in the 50-mg group and 44% of patients in the 200-mg group had exposure-based dose adjustments before Week 12, resulting in mean Miri doses of 100 mg and 250 mg, respectively.

TABLE 10

Overview of Adverse Events - Maintenance Period

| Number of Patients[b] | PBO SC Q4W (N = 13) n (%) | 200 mg Miri SC Q4W (N = 47) n (%) | 200 mg Miri SC Q12W (N = 45) n (%) | Miri Total (N = 92) n (%) | Total (N = 105) n (%) | p-value[a] Miri Q4W vs Miri Q12W |
|---|---|---|---|---|---|---|
| Deaths[c] | 0 (0.0) | 0 (0.0) | 0 (0.0) | 0 (0.0) | 0 (0.0) | >0.999 |
| SAEs | 0 (0.0) | 1 (2.1) | 1 (2.2) | 2 (2.2) | 2 (1.9) | >0.999 |
| Discontinuations from study due to an AE | 0 (0.0) | 0 (0.0) | 0 (0.0) | 0 (0.0) | 0 (0.0) | >0.999 |
| TEAEs | 7 (53.8) | 29 (61.7) | 21 (46.7) | 50 (54.3) | 57 (54.3) | 0.209 |
| TEAEs related to | 3 (23.1) | 15 (31.9) | 3 (6.7) | 18 (19.6) | 21 (20.0) | 0.003 |

TABLE 10-continued

Overview of Adverse Events - Maintenance Period

| Number of Patients[b] | PBO SC Q4W (N = 13) n (%) | 200 mg Miri SC Q4W (N = 47) n (%) | 200 mg Miri SC Q12W (N = 45) n (%) | Miri Total (N = 92) n (%) | Total (N = 105) n (%) | p-value[a] Miri Q4W vs Miri Q12W |
|---|---|---|---|---|---|---|
| study treatment by investigator[d] | | | | | | |

Abbreviations:
AE = adverse event;
Miri = mirikizumab;
n = number of patients with at least 1 adverse event per event type;
N = number of patients in the safety population;
PBO = placebo;
Q4W = every 4 weeks;
Q12W = every 12 weeks;
SAE = serious adverse event;
SC = subcutaneous;
TEAE = treatment-emergent adverse event;
vs = versus.
[a]Between-group comparisons were made using Fisher's Exact test. No adjustments for multiplicity were made.
[b]Patients may be counted in more than 1 category.
[c]Deaths were also included as SAEs and discontinuations due to AEs.
[d]Includes events that were considered related to study treatment as judged by the investigator.

TABLE 11

Overview of Adverse Events - Extension Induction and Extension Maintenance

| Number of Patients[a] | Extension Open-Label 600 mg Miri IV Q4W (N = 32) n (%) | Extension Open-Label 1000 mg Miri IV Q12W (N = 95) n (%) | Extension Open-Label 200 mg Miri SC Q4W (N = 44) n (%) |
|---|---|---|---|
| Deaths[b] | 0 (0.0) | 0 (0.0) | 0 (0.0) |
| SAEs | 1 (3.1) | 5 (5.3) | 1 (2.3) |
| Discontinuations from study due to an AE | 0 (0.0) | 3 (3.2) | 0 (0.0) |
| TEAEs | 17 (53.1) | 38 (40.0) | 23 (52.3) |
| TEAEs related to study treatment by investigator[c] | 4 (12.5) | 9 (9.5) | 2 (4.5) |

Abbreviations: AE = adverse event; IV = intravenous; Miri = mirikizumab; n = number of patients with at least 1 adverse event per event type; N = number of patients in the safety population; Q4W = every 4 weeks; Q12W = every 12 weeks; SAE = serious adverse event; SC = subcutaneous; TEAE = treatment-emergent adverse event.
[a]Patients may be counted in more than 1 category.
[b]Deaths were also included as SAEs and discontinuations due to AEs.
[c]Includes events that were considered related to study treatment as judged by the investigator.

Results: Pharmacokinetics (PK) and Exposure/Response Modelling i) Summary of Population PK Analyses A total of 2828 serum mirikizumab concentration samples were taken from 229 patients during the induction, maintenance and extension periods and were used in the PK analysis. The concentration data was analyzed using population PK methods. A 2-compartment model with first-order absorption for the SC maintenance doses was found to best describe the PK of mirikizumab. The estimated typical population clearances was 0.023 L/hr (2.8% SD of the estimate (SEE)), and random between-patient variability in apparent clearance was 32% (% CV). The estimated SC bioavailability was 42%.

The estimated typical population values for central and peripheral volumes of distribution and intercompartmental clearance were 3.5 L, 1.4 L and 0.0064 L/hr, respectively. A total of 303 samples (9%) were below the lower limit of quantitation of the mirikizumab assay (100 ng/mL). Excluding these samples was compared to standard imputation or conditional estimation models in the PK modeling and no impact on the estimated PK parameters was noted.

FIG. 1 shows the average serum concentration of mirikizumab calculated using the PK model-estimated individual patient clearance values, along with a reference line indicating where the median average concentration would be expected for a 300-mg IV fixed dose.

The population PK model was used to evaluate the impact of the following covariates: age, gender, BMI, body weight, ethnic origin, dose level, smoking status, site of injection, prior biologic status, baseline albumin, time-varying albumin, baseline CRP, baseline fecal calprotectin, baseline MMS, baseline RB subscore, extent of disease, an immunogenicity (ADA+/−, TE-ADA+/−, ADA titer, neutralizing ADA+/−). The only factors that were found to have a statistically significant impact were time-varying albumin on clearance and body weight on central volume of distribution.

ii) Summary of Observed Concentrations during Maintenance

In the 200-mg mirikizumab SC Q4W group, the first sample was collected 2 to 10 days after the first dose, and all subsequent samples were collected prior to dosing and thus represent trough concentrations. The Q4W regimen produced trough concentrations that were consistent over the maintenance period. These trough concentrations were similar to the trough concentrations observed in the 200-mg mirikizumab IV induction group at Week 12 in the induction period.

In the 200-mg mirikizumab SC Q12W group, the first sample was also collected 2 to 10 days after the first dose, and subsequent samples were collected at 4, 8 or 12 weeks after dose. Samples collected at Weeks 24, 48 and 72 were taken prior to dose administration and represent trough concentrations. Most patients in this dose group had concentrations that were below the quantitation limit (BQL) at trough. This was expected based on the long interval between doses. The SC Q12W regimen produced a more intermittent concentration profile than the Q4W regimen.

iii) Summary of Observed Exposure—Response Data

FIG. 2 shows the observed clinical response, clinical remission, endoscopic response, and symptomatic response versus the median of the average concentration in each induction group. Exposure increased in a dose-proportional manner. The mean exposure-response relationships for the plotted endpoints followed the same general pattern, with rates increasing between the placebo and 50-mg groups, and between the 50-mg and 200-mg groups, but then decreasing between the 200-mg and 600-mg groups.

FIG. 3 and FIG. 4 show the individual patient average concentrations or observed Week 12 concentrations, grouped by whether the patient achieved clinical response or remission. These plots show that there was significant overlap in the individual patient concentrations in patients who achieved response or remission versus those patients who did not achieve these endpoints. The plots also show that the lower efficacy observed in the 600-mg group was not due to low exposures in some patients, as patients in the 50-mg and 200-mg cohorts achieved clinical response and remission at exposures similar to or below the lowest individual patients in the 600-mg group. The patients with the lowest observed Week 12 concentrations in Tertile 1 and Tertile 2 in the 600-mg group that did not achieve remission are similar to the concentrations of patients who did achieve remission in the 50-mg and 200-mg groups.

iv) Summary of Model-Based Analyses

The relationship between exposure and efficacy was explored using the MMS. Direct evaluation of the MMS provides resolution of the exposure-efficacy relationship as it is a measure that has more levels as compared to the binary clinical response and remission endpoints. The MMS was evaluated using by evaluating the change from baseline to Week 12 in the MMS and patients with the greatest decrease from baseline in MMS are interpreted as having achieved the best efficacy. The following covariates were evaluated in the model: baseline albumin, baseline CRP, baseline fecal calprotectin, prior biologic treatment status, extent of disease, baseline MMS, baseline SF subscore, baseline RB subscore, baseline ES, smoking status, body weight, and whether the patient had an exposure-based dose adjustment.

The relationship between mirikizumab exposure and reduction in the MMS at Week 12 indicates that doses below 300 mg may lead to decreased efficacy, and a dose of 300 mg would produce 91% of the maximal effect possible with mirikizumab. Furthermore, a dose of 300 mg is expected to produce a median average concentration that covers the majority of individual patient exposures that were observed in the 200-mg cohort in the study (see FIG. 5).

In the maintenance period, a more consistent concentration profile was observed with the Q4W dose regimen as compared to the Q12W regimen, which produced a more intermittent concentration profile. The Q4W regimen also produced trough concentrations that were similar to the Week 12 trough concentration produced in the 200-mg induction group that achieved the best efficacy. Patients who achieved clinical response or clinical remission at Week 52 also tended to have higher maintenance concentrations. These results suggest that a 200-mg SC Q4W regimen is more likely to provide better maintenance efficacy than a 200-mg Q12W regimen.

Example 2: Clinical Study

Part A

Overview

This study is a multicenter, randomized, double-blind, parallel-arm, placebo-controlled study designed to evaluate the safety and efficacy of mirikizumab, compared with placebo, over a 12-week induction period. The study population includes patients with moderately to severely active UC who have an inadequate response to, loss of response to, or are intolerant to corticosteroid or immunomodulator therapy for UC (termed "conventional-failed" in this study), and those who have an inadequate response to, loss of response to, or are intolerant to biologic therapy for UC (termed "biologic-failed" in this study). Patients who complete Part A through Week 12 will either complete post-treatment follow-up within Part A or be eligible to participate in Part B.

Patients who discontinue treatment prior to the Week 12 assessment, or those who are unable or are not willing to participate in Part B will complete post-treatment follow-up 16 weeks after their last visit. The study comprises of a screening period of up to a maximum of 28 days, and a 12-week blinded intravenous therapy period.

Objectives

The primary objective is to test the hypothesis that mirikizumab is superior to placebo in inducing clinical remission at Week 12 in patients with moderately to severely active ulcerative colitis (UC).

Secondary objectives include the following:
  To evaluate the efficacy of treatment with mirikizumab compared to placebo in inducing a clinical response at Week 12;
  To evaluate the efficacy of treatment with mirikizumab compared to placebo in inducing endoscopic remission at Week 12;
  To evaluate the efficacy of treatment with mirikizumab compared to placebo in inducing symptomatic remission at Weeks 4 and 12;
  To evaluate the efficacy of treatment with mirikizumab compared to placebo in inducing clinical response in the biologic-failed population at Week 12; and
  To evaluate the time to symptomatic response and the time to symptomatic remission.

Endpoints were defined using the MMS. Endoscopies are read centrally. Rates of endoscopic healing are also determined at Week 12. The endpoint definitions are as follows:
  Clinical remission: Having achieved the following MMS subscores: a rectal bleeding (RB) subscore of 0, stool frequency (SF) subscore of 0 or 1 (with ≥1-point decrease from baseline), and endoscopic subscore (ES) of 0 or 1 (excluding friability).
  Clinical response: Having achieved a decrease in 9-point Mayo subscore of ≥2 points and ≥30% from baseline, with either a decrease of RB subscore of ≥1 or a RB subscore of 0 or 1.
  Endoscopic remission: Having achieved a Mayo ES of 0.
  Endoscopic healing: Having achieved a Mayo ES of 0 or 1.
  Symptomatic remission: SF=0, or SF=1 with a ≥1-point decrease from baseline, and RB=0.
  Symptomatic response: at least a 30% decrease from baseline in composite SF and RB.

Methods

This study comprises a screening period and a 12-week blinded intravenous induction period.

a) Screening Period

Patients are evaluated for study eligibility ≤28 days before the baseline visit. At the baseline visit, patients who fulfill the eligibility criteria are randomized equally to 1 of 4 induction treatment arms.

Eligible patients are male or female patients aged 18-80 years at the time of initial screening. Patients must have:
- i) an established diagnosis of UC of ≥3 months in duration before baseline (Week 0), which includes endoscopic evidence of UC and a histopathology report that supports a diagnosis of UC;
- ii) moderately to severely active UC as defined by a modified Mayo score (MMS) of 4 to 9 with an endoscopic subscore (ES)≥2, with endoscopy performed within 10 days before baseline;
- iii) evidence of UC extending proximal to the rectum (distal to the rectosigmoid junction, which lies approximately 10-15 cm from anal margin).
- iv) documentation of:
  - a) a surveillance colonoscopy (performed according to local standard) within 12 months before baseline for:
    - patients with pancolitis of >8 years' duration, or
    - patients with left-sided colitis of >12 years' duration, or
    - patients with primary sclerosing cholangitis.
  - OR
  - b) in patients for whom a) does not apply, up-to-date colorectal cancer surveillance (performed according to local standard). At the discretion of the investigator, a colonoscopy (instead of a flexible sigmoidoscopy) can be performed as the screening endoscopy for this study. Patients who do not have a colonoscopy report available in source documentation will have a colonoscopy at screening.

Patients may be receiving a therapeutic dosage of the following drugs:
- (a) oral 5-ASA compounds: if the prescribed dose has been stable for at least two weeks before baseline;
- (b) oral corticosteroid therapy prednisone≤20 mg/day or equivalent, or budesonide extended release tablets 9 mg/day [budesonide MMX]); if the prescribed dose has been stable for at least 2 weeks before the screening endoscopy; or
- (c) AZA, 6-MP and methotrexate: if these immunomodulators have been prescribed at a stable dose for at least 8 weeks before the screening endoscopy.

b) Induction Period

This study involves a comparison of IV administration of mirikizumab versus placebo during a 12-week induction period:

| Treatment Group | Description |
| --- | --- |
| Mirikizumab Dose Arm 1 | 300 mg given as an intravenous infusion (Weeks 0, 4, 8) |
| Control | Placebo given as an intravenous infusion (Weeks, 0, 4, 8) |

IV infusion of mirikizumab or placebo will occur over at least 30 minutes.

The primary endpoint is clinical remission at Week 12 (mirikizumab versus placebo). Clinical remission is based on the MMS.

The MMS and the composite SF and RB score, derived from assessment of the Mayo score are used to determine the major secondary endpoints.

Part B

Overview

Part B is a multicenter, randomized, double-blind, placebo-controlled, parallel-arm study evaluating the safety and efficacy of 200 mg mirikizumab Q4W SC in maintaining treatment response at Week 40 (that is, in combination with Part A, 52 weeks of continuous therapy). The study population includes patients with moderately to severely active UC who completed Part A. Part A includes patients who have an inadequate response to, loss of response to, or are intolerant to conventional (non-biologic) therapy for UC ("conventional-failed"), and those who have an inadequate response to, loss of response to, or are intolerant to biologic therapy for UC ("biologic-failed").

Patients who achieved clinical response with blinded mirikizumab treatment during Part A are randomized 2:1 to blinded 200 mg mirikizumab Q4W SC or blinded placebo. Patients who responded to blinded placebo in their induction study remain on blinded placebo in Part B. Open-label rescue therapy with 300 mg mirikizumab Q4W intravenous (IV) is administered for 3 doses if patients lose response.

Patients who did not achieve clinical response with either blinded mirikizumab or blinded placebo during Part A receive open-label extended induction therapy with 300 mg mirikizumab Q4W IV administered for 3 doses. Patients who achieve delayed clinical response (defined using induction study baseline) receive open-label 200 mg mirikizumab Q4W SC. Extended induction study non-responders who do not achieve clinical response at Week 12 of Part A are discontinued.

Objectives

The primary objective is to test the hypothesis that mirikizumab is superior to placebo in maintaining clinical remission at Week 40 (Week 52 of continuous therapy) among patients induced into clinical remission with mirikizumab. This involves determining the proportion of patients who were in clinical remission at Week 12 in Part A and are in clinical remission at Week 40, that is, with durable clinical remission.

Secondary objectives include the following:
- To evaluate the efficacy of mirikizumab compared to placebo in achieving clinical remission at Week 40 among patients induced into clinical response with mirikizumab.
- To evaluate the efficacy of mirikizumab compared to placebo on endoscopic remission at Week 40 among patients induced into clinical response with mirikizumab.
- To evaluate the efficacy of mirikizumab compared to placebo in achieving corticosteroid-free remission without surgery among patients induced into clinical response with mirikizumab and receiving corticosteroids at induction baseline.
- To evaluate, in the subgroup of patients in whom biologic agents have failed or caused intolerance, clinical remission at Week 40 among patients induced into clinical response with mirikizumab.
- To evaluate, in the subgroup of patients in whom biologic agents have failed or caused intolerance, endoscopic remission at Week 40 among patients induced into clinical response with mirikizumab.
- To evaluate, in the subgroup of patients in whom biologic agents have failed or caused intolerance, clinical remission at Week 40 among patients induced into clinical remission with mirikizumab.
- To evaluate the efficacy of mirikizumab compared to placebo in achieving corticosteroid-free remission without surgery among patients induced into clinical remission with mirikizumab and receiving corticosteroids at induction baseline.

Endpoints are defined using the MMS. Endoscopies are read centrally. Rates of endoscopic healing are also determined at Week 52. The endpoint definitions are as follows:

Clinical remission: Having achieved the following MMS subscores: a rectal bleeding (RB) subscore of 0, stool frequency (SF) subscore of 0 or 1 (with □ 1 point decrease from baseline), and endoscopic subscore (ES) of 0 or 1 (excluding friability).

Clinical response: Having achieved a decrease in 9 point Mayo subscore of ≥2 points and ≥30% from baseline, with either a decrease of RB subscore of ≥1 or a RB subscore of 0 or 1.

Endoscopic remission: Having achieved a Mayo ES of 0.

Endoscopic healing: Having achieved a Mayo ES of 0 or 1.

Symptomatic remission: SF=0, or SF=1 with a ≥1-point decrease from baseline, and RB=0.

Symptomatic response: at least a 30% decrease from baseline in composite SF and RB.

Corticosteroid-free remission without surgery is defined as:
Clinical remission; and
No corticosteroid use for ≥12 weeks prior to assessment Methods Patient Population Patients with moderately to severely active UC who completed Part A and who meet eligibility requirements are enrolled in this study. The study enrolls patients who achieve clinical response or clinical remission with blinded mirikizumab or placebo dosing in Part A, as well as patients who do not achieve clinical response with blinded mirikizumab or placebo during Part A.

Treatment Assignments

Maintenance study treatment assignment is dependent on whether patients responded to study drug dosing in Part A and whether they experience a loss of response (LOR) during this study as follows:

i) Mirikizumab Responders from Part A

Patients who achieve clinical response with blinded mirikizumab in Part A are randomized to receive blinded 200 mg mirikizumab Q4W SC or blinded placebo SC Q4W (randomized withdrawal) in a 2:1 ratio. Randomization is stratified to achieve between-group comparability, based on biologic-failed status (yes or no), induction remission status (yes or no), corticosteroid use (yes or no), and region (North America/Europe/Other). Patients will continue on the randomized treatment assignment for the remainder of Part B unless they develop secondary LOR.

Loss of Response (LOR) is defined as:
≥2-point increase from Part B baseline in the combined SF+RB scores;
combined SF+RB score of ≥4, on 2 consecutive visits (≥7 days apart, and with confirmation of negative C. difficile testing); and
Confirmed by centrally read endoscopic subscore (ES) of 2 or 3

SC dosing is continued according to dosing schedule until endoscopy determines whether LOR is confirmed. If LOR is confirmed based on endoscopy at or after Week 12 (and C. difficile stool toxin testing is negative), patients are rescued with open-label 300 mg mirikizumab Q4W IV for 3 doses. The first IV rescue dose may be administered as soon as LOR is confirmed by centrally read endoscopy, if ≥7 days from the most recent SC dose. Subsequent doses will be given every 4 weeks for total of 3 doses.

If endoscopy does not confirm secondary LOR, patients continue SC study drug dosing, maintaining the scheduled dosing interval. If study drug dosing is continued, an additional endoscopy is performed at Week 40, early termination visit (ETV) or unscheduled visit (UV).

Patients who, in the opinion of the investigator, receive clinical benefit after completion of the LOR rescue therapy (12 weeks after first IV rescue dose) are considered for enrollment into the long term extension study Part C to receive further SC dosing. Once the LOR IV rescue therapy is initiated, no further SC dosing is available in Part B.

ii) Placebo Responders from Part A

Patients who achieve clinical response with blinded placebo in Part A continue to receive blinded placebo for the remainder of the maintenance study. Placebo SC injections are administered Q4W to maintain study blind. If LOR is confirmed based on endoscopy at or after Week 12 (and C. difficile stool toxin testing is negative), patients are rescued with open-label mirikizumab 300 mg Q4W IV for 3 doses. The same LOR assessments and procedures should be performed as described for the mirikizumab responders from Part A.

iii) Mirikizumab and Placebo Non-responders from Part A

Patients who do not achieve clinical response to blinded mirikizumab or blinded placebo in Part A receive open-label extended induction therapy with 300 mg mirikizumab IV at Weeks 0, 4, and 8, and undergo endoscopy at Week 12.

Patients who achieve delayed clinical response (compared to induction study baseline) with extended mirikizumab induction therapy at Week 12 subsequently receive open-label 200 mg mirikizumab Q4W SC starting at Week 12. Patients continue on this dose regimen and undergo endoscopy at Week 40.

Patients who, in the opinion of the investigator, receive clinical benefit may be considered for enrollment into the long term extension study Part C to receive further SC dosing.

Patients who do not achieve clinical response to mirikizumab IV extended induction therapy at Week 12, compared to induction baseline, discontinue study drug and undergo procedures for early termination of the study drug, including post-treatment follow-up.

iv) Post-Treatment Follow-up Period

Patients will undergo a maximum 16-week post-treatment follow-up period:
Patients who discontinue study drug with last dose administered IV return for post-treatment follow-up visits at 4 and 16 weeks after the end-of-treatment visit.
Patients who discontinue study drug with last dose administered SC return for post-treatment follow-up visits at 4 and 12 weeks after the end-of-treatment visit.
Patients who subsequently enter the long term extension study Part C do not need to complete the post-treatment follow-up period.

Part C

Overview

Part C is a single-arm, outpatient, open-label, multicenter, long-term extension study evaluating the efficacy and safety of mirikizumab in patients with moderately to severely active UC who have participated in an originator mirikizumab UC study, including, but not limited to, the study described in Example 1 and Part B.

Objectives

The primary objective is to evaluate the long-term efficacy of mirikizumab. A secondary objective is to evaluate the effect of long term mirikizumab therapy on histologic remission (mucosal healing).

Methods

Patients from the Example 1 study and Part B are eligible for enrollment into Part C.

Patient Population

The Example 1 study is a randomized, double-blind, placebo-controlled study investigating the efficacy and safety of mirikizumab in patients with moderate-to-severe UC. The study consists of a 12-week double-blind induction period followed by either a maintenance period (up to 144 weeks) or an extension period (12 weeks extension induction, up to 132 weeks extension maintenance) for up to 156 weeks total. Study patients eligible for consideration for enrollment into Part C include the following:

Patients who complete the maintenance period Week 52 endoscopy visit and the assessments at the end of study/early termination visit, or Patients who complete the extension period Week 40 endoscopy visit and the assessments at the end of study/early termination visit.

At the time of their last Example 1 study visit, a patient may be receiving blinded mirikizumab 200 mg SC Q4W, blinded mirikizumab 200 mg SC Q12W, blinded placebo SC Q4W, or unblinded (open label) mirikizumab 200 mg SC Q4W. Patients receiving blinded placebo SC at the time of their last visit in the Example 1 study will receive mirikizumab for the first time in Part C.

Part B is a randomized, double-blind, placebo-controlled study evaluating the efficacy and safety of 200 mg mirikizumab administered SC Q4W in maintaining treatment response at Week 40 (Week 52 of continuous therapy) in patients with moderately to severely active UC who completed 12 weeks of induction treatment. Part B patients eligible for consideration for enrollment into AMAP include the following:

Patients who complete Week 40 visit on blinded SC mirikizumab or placebo therapy without experiencing loss of response (LOR) during Part B Patients who complete Week 40 visit on open-label SC mirikizumab after responding to re-induction with IV mirikizumab Patients who complete Part B early termination visit after receiving IV rescue for LOR and who had clinical benefit at the time of their last Part B visit, A patient may be receiving blinded mirikizumab 200 mg SC Q4W, blinded placebo SC Q4W, open-label (unblinded) mirikizumab 300 mg IV, or open-label mirikizumab 200 mg SC Q4W. Patients receiving blinded placebo SC at the time of their last visit in Part B will be receiving mirikizumab for the first time in Part C.

Study Treatment

Mirikizumab 200 mg are administered subcutaneously every 4 weeks. Patients receive open-label mirikizumab in Part C, regardless of whether they were receiving blinded or unblinded (open-label) mirikizumab or blinded placebo when their participation ended in the originating study. No rescue with mirikizumab is available during Part C.

Endoscopy is performed at Week 52 (Year 1), Week 100 (Year 2), and Week 160 (Year 3) of Part C. The last endoscopy performed in the originator study may be used as baseline for Part C. Patients from Part C who have not had endoscopy performed within 8 months of Week 0 of Part C have an endoscopy performed at Week 0. Patients with pancolitis of >8 years' duration, left-sided colitis of >12 years' duration, or primary sclerosing cholangitis require colorectal cancer surveillance colonoscopy for UC-associated dysplasia and malignancy. Patients with a family history of colorectal cancer, personal history of increased colorectal cancer risk, age>50 years, or with other known risk factors also require colonoscopy for colorectal cancer surveillance.

The invention claimed is:

1. A method of treating ulcerative colitis (UC) comprising administering to a patient in need thereof an anti-IL-23p19 antibody, wherein the anti-IL-23p19 antibody is mirikizumab, said method comprising:
    a) administering three induction doses of mirikizumab to the patient by intravenous infusion at 4 week intervals, wherein each induction dose comprises 300 mg of mirikizumab; and
    b) administering maintenance doses of mirikizumab to the patient by subcutaneous injection at 4 week or 12 week intervals, wherein the first maintenance dose is administered 2-8 weeks after the last induction dose is administered and wherein each maintenance dose comprises 200 mg of mirikizumab.

2. The method of treating UC according to claim 1, wherein the first maintenance dose is administered 4-6 weeks after the last induction dose is administered.

3. The method of treating UC according to claim 2, wherein subsequent maintenance dose(s) of mirikizumab are administered at 4 week intervals after administration of the first maintenance dose.

4. The method of treating UC according to claim 2, wherein subsequent maintenance dose(s) of mirikizumab are administered at 12 week intervals after administration of the first maintenance dose.

5. The method of treating UC according to claim 1, wherein subsequent maintenance dose(s) of mirikizumab are administered at 4 week intervals after administration of the first maintenance dose.

6. The method of treating UC according to claim 1, wherein subsequent maintenance dose(s) of mirikizumab are administered at 12 week intervals after administration of the first maintenance dose.

7. The method of treating UC according to claim 1, wherein the patient is biologic-naïve, biologic-experienced, biologic-failed, or is conventional failed.

* * * * *